United States Patent
Huttner et al.

Patent Number: 6,166,234
Date of Patent: Dec. 26, 2000

[54] TRIPODAL CYCLOPENTADIENE DERIVATIVES AND THEIR USE

[75] Inventors: Gottfried Huttner, Heidelberg; Joachim Vogelgesang, Mannheim; Ute Winterhalter, Walldorf; Björn Antelmann, Celle, all of Germany

[73] Assignee: BASF Aktiengesellschaft, Ludwigshafen, Germany

[21] Appl. No.: 09/006,174

[22] Filed: Jan. 13, 1998

[30] Foreign Application Priority Data

Jan. 21, 1997 [DE] Germany .................. 197 01 866

[51] Int. Cl.⁷ ................................................. C07F 9/02
[52] U.S. Cl. .................. 556/15; 556/11; 556/81; 556/87; 556/413; 556/430; 556/435; 564/305; 564/395; 564/426; 564/428; 564/445; 564/450; 564/454; 564/455; 564/460; 568/13
[58] Field of Search .................. 556/81, 87, 413, 556/430, 435, 15, 11; 564/305, 395, 428, 426, 445, 450, 454, 455, 460; 568/13

[56] References Cited

U.S. PATENT DOCUMENTS

| | | | |
|---|---|---|---|
| 5,057,300 | 10/1991 | Lilga et al. | 423/648.1 |
| 5,118,855 | 6/1992 | Baan et al. | 568/13 |
| 5,254,707 | 10/1993 | Strickler et al. | 556/413 |
| 5,268,495 | 12/1993 | Riepl | 556/11 |

FOREIGN PATENT DOCUMENTS

| | | |
|---|---|---|
| 2242189 | 9/1991 | United Kingdom . |
| 97/42162 | 11/1997 | WIPO . |

OTHER PUBLICATIONS

Heidel et al., *Anorganische Chemie, Organische Chemie.*, vol. 48, No. 11, Nov. 1993, pp. 1681–1692.
Fryzuk et al., *J. Amer. Chem. Soc.*, vol. 115, No. 12, pp. 5336–5337.
Bensley et al., *J. of Org. Chem.*, vol. 53, No. 18, Mar. 1988, pp. 4417–4419.
Antelmann et al., *J. of Org. Chem.*, vol. 545–546, 1997, pp. 407–420.

*Primary Examiner*—James O. Wilson
*Attorney, Agent, or Firm*—Keil & Weinkauf

[57] ABSTRACT

Novel tripodal cyclopentadiene derivatives have the formula (I)

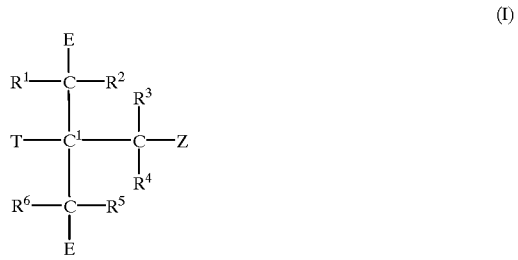

where

E are identical or different and are —N(R)(R), —P(R)(R), —As(R)(R), —Sb(R)(R), —OR, —SR, —SeR, —TeR, where R are identical or different and are each hydrogen, a $C_1$–$C_{20}$-carboorganic radical or a $C_1$–$C_{30}$-organosilicon radical, or E is a leaving group X and $R^1$, $R^2$, $R^3$, $R^4$, $R^5$, $R^6$ are identical or different and are each hydrogen, a $C_1$–$C_{20}$-carboorganic radical or a $C_1$–$C_{30}$-organosilicon radical, Z is a cyclopentadienyl radical or a substituted cyclopentadienyl structural unit and T is hydrogen, a $C_1$–$C_{20}$-carboorganic radical or a $C_1$–$C_{30}$-organosilicon radical or a group E—Y—, where E is —N(R)(R), —P(R)(R), —As(R)(R), —Sb(R)(R), —OR, —SR, —SeR, —TeR or a leaving group X, where R are identical or different and are each hydrogen, a $C_1$–$C_{20}$-carboorganic radical or a $C_1$–$C_{30}$- organosilicon radical and Y is a $C_1$–$C_{20}$-organic group which connects E to $C^1$.

16 Claims, No Drawings

TRIPODAL CYCLOPENTADIENE DERIVATIVES AND THEIR USE

The present invention relates to tripodal cyclopendadiene derivatives of the formula (I)

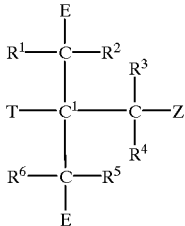
(I)

where

E are identical or different and are —N(R)(R), —P(R)(R), —As(R)(R), —Sb(R)(R), —OR, —SR, —SeR, —TeR, where R are identical or different and are each hydrogen, a $C_1$–$C_{20}$-carboorganic radical or a $C_1$–$C_{30}$-organosilicon radical, or E is a leaving group X and $R^1$, $R^2$, $R^3$, $R^4$, $R^5$, $R^6$ are identical or different and are each hydrogen, a $C_1$–$C_{20}$-carboorganic radical or a $C_1$–$C_{30}$-organosilicon radical, Z is a cyclopentadienyl radical or a substituted cyclopentadienyl structural unit and T is hydrogen, a $C_1$–$C_{20}$-carboorganic radical or a $C_1$–$C_{30}$-organosilicon radical or a group E—Y—, where E is —N(R)(R), —P(R)(R), —As(R)(R), —Sb(R)(R), —OR, —SR, —SeR, —TeR or a leaving group X, where R are identical or different and are each hydrogen, a $C_1$–$C_{20}$-carboorganic radical or a $C_1$–$C_{30}$- organosilicon radical and Y is a $C_1$–$C_{20}$-organic group which connects E to $C^1$, Furthermore, the present invention relates to processes for preparing tripodal cyclopentadiene derivatives (I) and the use of the compounds (I) as ligands in metal complexes, also tripod metal complexes of the formula (V)

$$L_nM(T_p)_m \quad (V)$$

where

M is a transition metal or a main group metal of the Periodic Table of the Elements, $T_p$ is a singly deprotonated cyclopentadiene derivative of the formula (I)

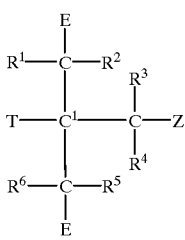
(I)

where

E are identical or different and are —N(R)(R), —P(R)(R), —As(R)(R), —Sb(R)(R), —OR, —SR, —SeR, —TeR, where R are identical or different and are each hydrogen, a $C_1$–$C_{20}$-carboorganic radical or a $C_1$–$C_{30}$-organosilicon radical, or E is a leaving group X and $R^1$, $R^2$, $R^3$, $R^4$, $R^5$, $R^6$ are identical or different and are each hydrogen, a $C_1$–$C_{20}$-carboorganic radical or a $C_1$–$C_{30}$-organosilicon radical, Z is a cyclopentadienyl radical or a substituted cyclopentadienyl structural unit and T is hydrogen, a $C_1$–$C_{20}$-carboorganic radical or a $C_1$–$C_{30}$-organosilicon radical or a group E—Y—, where E is —N(R)(R), —P(R)(R), —As(R)(R), —Sb(R)(R), —OR, —SR, —SeR, —TeR or a leaving group X, where R are identical or different and are each hydrogen, a $C_1$–$C_{20}$-carboorganic radical or a $C_1$–$C_{30}$- organosilicon radical and Y is a $C_1$–$C_{20}$-organic group which connects E to $C^1$, L is a formally anionic or uncharged ligand, or identical or different ligands of this type, n is an integer from 0 to 7, m is an integer from 1 to 8 and the use of these complexes for stoichiometric or catalytic carbon-carbon bond formation or hydrogenation.

Substituted cyclopentadienyl compounds are important ligands in transition metal catalysis. An example from polymer chemistry is metallocene catalysts, H. H. Brintzinger, D. Fischer et al., Angew. Chem. (1995), pages 1255 to 1283.

The structure and chemical constitution of the ligands have a great influence on the catalytic properties of the metal complexes obtainable with them.

For example, it is known from J. A. Ewen et al., Makromol. Chem. Makromol. Symp. 48/49 (1991), pp. 253–295 that the ligand structure in metallocenes (complexes of metals with at least one cyclopentadienyl-type ligand) which are constituents of catalysts for olefin polymerization can exert an influence on the polymer properties.

Since industry is demanding new, improved plastics, active compounds and effect chemicals which can be obtained only to a limited extent using known ligands and catalyst systems, there is a requirement for preparing new compounds suitable as ligands in catalytically active metal complexes.

It is an object of the present invention to provide novel cyclopentadiene derivatives which additionally have donor centers which have a structure different from the cyclopentadiene structure and which may, if desired, be able to be physically or particularly chemically fixed via a further functionality (anchor group or lyophilizing group), for example to a support material, and are suitable as ligands in metal complexes. A further object of the present invention is to provide chiral compounds which can be used as ligands for chiral, catalytically active metal complexes or chiral metal complexes in catalyst systems.

We have found that this object is achieved by the tripodal cyclopentadiene derivatives (I) defined in the introduction, processes for their preparation and also the use of (I) as ligands in metal complexes or catalyst systems and also tripod metal complexes (V) and their use for stoichiometric or catalytic carbon-carbon bond formation or hydrogenation.

The substituents E in (I) are either identical or different. They are

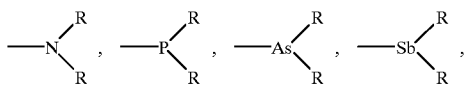

—OR, —SR, —SeR or —TeR, or a leaving group X such as chlorine, bromine, —OSO$_2$CH$_3$, OSO$_2$CF$_3$. E in (I) is preferably bromine,

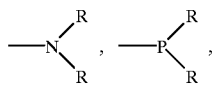

—OR, —SR and in particular

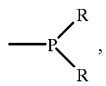

—OR, —SR or bromine.

The radicals R can be identical or different; they are preferably identical. R is hydrogen, a $C_1$–$C_{20}$-carboorganic radical or a $C_1$–$C_{30}$- organosilicon radical such as trimethylsilyl, triphenylsilyl.

In general, the chemical constitution of the radicals R is not critical. Preferred $C_1$–$C_{20}$-carboorganic radicals R are $C_1$–$C_{10}$-alkyl or $C_3$–$C_{10}$-cyclolakyl, for example methyl, ethyl, n-propyl, i-propyl, n-butyl, sec-butylf i-butyl, tert-butyl, n-pentyl, n-hexyl, n-octyl, n-decyl, cyclopropyl, cyclobutyl, cyclopentyl and cyclohexyl. Preferred radicals of this type are methyl, ethyl, cyclohexyl, in particular ethyl. Further very well suited radicals R are $C_6$–$C_{20}$-aryl radicals or $C_7$–$C_{20}$-arylalkyl or $C_7$–$C_{20}$-alkylaryl radicals having from 6 to 15 carbon atoms in the aryl radical. The aryl radicals may be substituted, for example by $C_1$–$C_{10}$-alkyl radicals or halogen atoms such as chlorine, bromine, iodine or fluorine, or else with other aryl radicals to form biphenyl radicals which may also be connected "ortho-ortho" to the heteroatom. Examples which may be mentioned are phenyl, benzyl, para-, ortho-, meta-xylyl, para-, meta-, ortho-tolyl or else mesityl, ortho-, meta-, para-chlorophenyl, ortho-, meta-, para-trifluoromethylphenyl.

Particularly preferred aromatic or aromatic-substituted radicals R are phenyl, meta-xylyl, 2,2'-biphenyldiyl, benzyl.

Particularly preferred substituents E are diphenylphosphino —P($C_6H_5$)$_2$, di(meta-xylyl)phosphino, 5-dibenzophospholyl

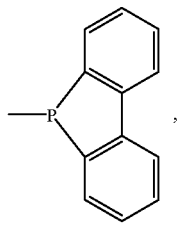

diethylphosphino —P($C_2H_5$)$_2$, thiobenzyl —S(CH$_2$C$_6$H$_5$).

The radicals $R^1$, $R^2$, $R^3$, $R^4$, $R^5$, $R^6$ are identical or different and are as defined above for R; $R^1$, $R^2$, $R^3$, $R^4$, $R^5$, $R^6$ are preferably hydrogen, methyl, ethyl, phenyl, in particular hydrogen.

The substituent Z in (I) is a $C_5$–$C_{50}$-cyclopentadienyl structural unit. For the purposes of the present invention, this includes the cyclopentadienyl radical itself ($C_5H_5$) and also all monocyclic and polycyclic, substituted or unsubstituted molecular structures having a total of from 5 to 50 carbon atoms in which the cyclopentadienyl structural unit is formally present. Examples which may be mentioned are cyclopentadiene derivatives which are monosubstituted to tetrasubstituted with $C_1$–$C_{20}$-carboorganic or $C_1$–$C_{30}$-organosilicon radicals R, where the definition and preferences for R are as defined above for R in (I). Examples which may be mentioned are methylcyclopentadienyl, tert-butylcyclopentadienyl.

Examples of polycyclic derivatives of the cyclopentadienyl structural unit are indenyl, fluorenyl, benzindenyl and also their derivatives which are monosubstituted to octasubstituted with $C_1$–$C_{20}$-carboorganic or $C_1$–$C_{30}$-organosilicon radicals R, where the definition and preferences for R are the same as defined for R in (I).

Preferred substituents z in (I) are cyclopentadienyl

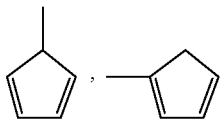

and other tautomers, indenyl

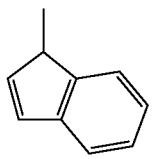

and other tautomers, fluorenyl

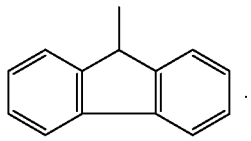

The group Z is generally bonded to the remainder of the molecule of the formula (I) via the cyclopentadienyl-type 5-membered ring of the group Z, where, owing to tautomerism in Z, (I) is generally present as a mixture of tautomers.

T in (I) is hydrogen, a $C_1$–$C_{20}$-carboorganic radical, a $C_1$–$C_{30}$-organosilicon radical or a group E—Y— where E is

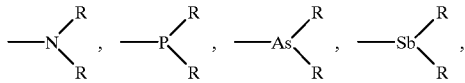

—OR, —SR, —SeR, —TeR or a leaving group X, where R is as defined above for E in (I).

Y is a $C_1$–$C_{20}$-organic group which connects E to $C^1$ in (I). Y is preferably a $C_1$–$C_{10}$-αω-alkanediyl unit, such as

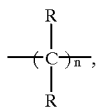

where R are identical or different and are each as defined above for R in (I), but in particular are hydrogen, and n is an integer from 1 to 10. Well suited structural units Y are 1,2-ethanediyl-CH$_2$—CH$_2$—, 1,3-propanediyl-CH$_2$—CH$_2$—CH$_2$—, in particular methylene—CH$_2$—.

A further preferred structural unit Y is represented by the following structural formula:

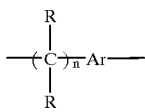

In this formula, R are identical or different and are as defined above in (I); it is preferred that both R are hydrogen; n is preferably 1. Ar is a $C_6$–$C_{20}$-aromatic structural unit, preferably $C_6R_4$, where R is as defined in (I) and is preferably hydrogen. The aryl radical is preferably para-disubstituted. A well suited structural unit is

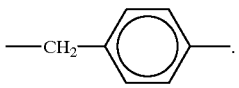

E in T is preferably RO— or a leaving group X, where R is as defined above in (I), preferably hydrogen or $C_1$–$C_{10}$-alkyl, $C_1$–$C_6$-aryl, formyl, acetyl, propionyl. The leaving group X is preferably fluorine, chlorine, iodine and in particular bromine, the methanesulfonyl radical $CH_3$—$SO_2$—, trifluoromethanesulfonyl radical $CF_3SO_2$— or p-toluenesulfonyl radical p-$(C_6H_4CH_3)$—$SO_2$—.

Well suited groups T are methyl, ethyl, phenyl, hydroxymethyl —$CH_2$—OH, acetylmethyl —$CH_2$—OC(O)$CH_3$, chloromethyl —$CH_2Cl$, bromomethyl —$CH_2Br$, mesylmethyl —$CH_2$—$OSO_2CH_3$.

Tripodal cyclopentadienes of the formula (I) in which all the groups bound to the carbon atom $C^1$ are different can be in the form of racemic mixtures, enantiomerically pure or as diastereomers, the latter generally when the groups bound to $C^1$ already have a center of chirality.

Suitable preparative methods for the tripodal cyclopentadienes (I) of the present invention generally start from the oxetane derivatives of the formula (II):

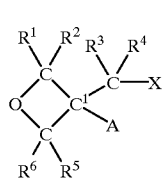

(II)

In this formula, the substituents $R^1, R^2, R^3, R^4, R^5, R^6$ are as defined above in (I). X is a leaving group in the sense of the definition given in a) Th. H. Lowry, K. Schueller Richardson, Mechanismen und Theorie in der Organischen Chemie, Verlag Chemie, Weinheim, 1980, p. 165, b) J. March, Advanced Organic Chemistry, 3rd ed., John Wiley & Sons, New York, 1985, p. 179. In general, all groups X whose conjugate acid HX is a strong acid are suitable as good leaving groups.

Such acids HX are, for example, hydrofluoric, hydrochloric, hydroiodic and preferably hydrobromic acids, also organic sulfonic acids such as methanesulfonic acid $CH_3$—$SO_3H$, p-toluenesulfonic acid p—$CH_3$—$C_6H_4$—$SO_3H$, trifluoromethanesulfonic acid $CF_3SO_3H$. The acids can be used as pure substances or else, preferably, in aqueous solution. In general, the hydrohalic acids are used in aqueous solution.

Good suitable leaving groups X are thus the substituents fluorine, chlorine, iodine and in particular bromine, also organic sulfonic acid derivatives such as the methanesulfonyl $CH_3$—$SO_3$—, p-toluenesulfonyl p-$C_6H_4$—$SO_3$—, trifluoromethanesulfonyl $CF_3$—$SO_3$— and benzenesulfonyl-$C_6H_5$—$SO_3$— groups.

A in (II) is hydrogen, a $C_1$–$C_{20}$-carboorganic radical or a $C_1$–$C_{30}$-organosilicon radical R having the definition of R in (I), or a structural unit —Y'X, where Y is a $C_1$–$C_{20}$-organic group which connects X to $C^1$. X is then a leaving group as defined above, preferably bromine or methanesulfonyl, p-toluenesulfonyl and Y is as defined above for (I).

The oxetane derivatives (II) are obtainable as described in
a) D. B. Pattison, J. Am. Chem. Soc., 1957, 79, 3455–3456,
b) J. Cheynd, P. Chabrier, J. Seyden-Penne, A. Habert-Somug, T. Strazalko, Bull. Soc. Chim., Fr. 1965, 694–700;
G. Huttner et al., Z. Naturforsch. 1995, 50b, 1045. They can be reacted via various reaction routes, here denoted as route 1 and route 2, to give the tripodal cyclopentadiene derivatives (I) of the present invention.

Route 1 is generally selected when the substituent A in (II) is virtually inert, ie. contains no groups which are accessible to nucleophilic substitution. Route 1 is therefore preferably selected when A in (II) is hydrogen, a $C_1$–$C_{20}$-carboorganic radical or a $C_1$–$C_{30}$-organosilicon radical; examples of substituents A are hydrogen, methyl, ethyl, n-propyl, i-propyl, n-butyl, sec-butyl, tert-butyl, i-butyl, cyclohexyl, benzyl, phenyl, trimethylsilyl, preferably methyl.

The oxetane derivatives (II) having inert substituents are then reacted via route 1 with one cyclopentadienide anion equivalent or one substituted cyclopentadienide anion equivalent. These are generally obtained by converting the parent cyclopentadiene $C_5H_6$ or its derivatives Z—H, where Z is as defined above for (I), into the corresponding metallated cyclopentadienide derivatives $(Z)_n\text{MetHal}_m$, where Met is lithium, sodium, potassium, rubidium, cesium, beryllium, magnesium, calcium, strontium, barium, boron, aluminum, gallium, indium or thallium, using known methods, for example by reaction with metal alkyl compounds such as butyllithium or ethylmagnesium chloride. Met is preferably lithium, magnesium and Hal is fluorine, bromine, iodine and in particular chlorine. n is 1,2 or 3, m is 0, 1 or 2 and the sum m+n is the formal valence of Met in $(Z)_n\text{MetHal}_m$.

The reaction of (II) with the cyclopentadienide anion equivalent is generally carried out in organic solvents such as alkanes, tetrahydrofuran, dioxane or mixtures thereof at from 50° C. to 100° C. In general, the reaction mixture is then hydrolyzed. The reaction mixture can be directly used further or else can be worked up to give the pure product (IIa), where $R^1$ to $R^6$ and Z are as defined for (I) and A is preferably inert and is defined in (II).

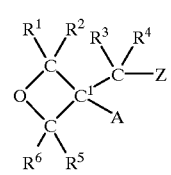

(IIa)

(IIa) can now be converted into the tripodal cyclopentadiene derivatives by two different routes.

In route 1a), (IIa) is generally reacted with an acid H-X which has been defined above and the oxetane ring is opened to give the compound (IIba) or (IIbb), or a mixture thereof, depending on the regioselectivity of the reaction

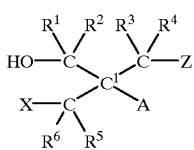

(IIba)

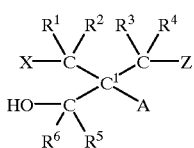

(IIbb)

In these formulae, the substituents $R^1$ to $R^6$, Z and X are as defined above in (I) and the substituent A is as defined above in (II).

The conversion of (IIa) into (IIba) or (IIbb) is generally carried out in an aliphatic, aromatic or ether solvent, for example hexane, toluene, ether, tetrahydrofuran or a mixture thereof at from −100 to 100° C., preferably from −100 to 0° C. A particularly preferred reagent H—X is aqueous hydrobromic acid. The product mixture obtained is usually worked up in a basic aqueous medium and can be directly processed further or else be purified by customary methods of preparative organic chemistry.

The compounds (IIba) and (IIbb) are valuable intermediates since, on the one hand, they can themselves act as ligand and, on the other hand, they can be further converted into a broad range of derivatives.

In derivative formation, the OH function in (IIba) or (IIbb) is converted into a leaving group X using the customary methods of organic chemistry. This is preferably achieved by reacting (IIba) or (IIbb) with a sulfonic acid derivative such as methanesulfonyl chloride, trifluoromethanesulfonyl chloride or p-toluenesulfonyl chloride to give (IIc), where X can be identical or different depending on the nature of the reagents used in the synthetic sequence for introducing the leaving group X and the radicals $R^1$ to $R^6$, Z, X are as defined in (I) and the radical A is as defined in (II).

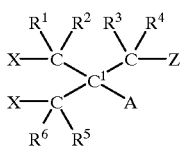

(IIc)

An alternative synthetic route to racemic or enantiomerically pure compounds of the formula (IIc) starts from a racemic or enantiomerically pure precursor of IIc in which Z is substituted by a leaving group X, as defined, and all X are different (IIc-1). A preferred compound of this type is racemic or enantiomerically pure $CH_3C(CH_2Br)(CH_2Cl)$ $CCH_2OSO_2CF_3$) which is obtainable, for example, as described by G. Huttner et al., Chem. Ber. 1994, pp. 271–274 and Z. Naturforsch. 1995, 50b, pp.729–734. Reaction of (IIc-1) with an above-defined cyclopentadienide anion equivalent of $(Z)_nMetHal_m$, preferably $C_5H_5Li$, $C_5H_5K$, then leads to a compound (IIc) which can be in the form of a racemate or be enantiomerically pure.

Reaction of (IIc) with $Met(E)_n$, where Met is lithium, sodium, potassium, rubidium, cesium, calcium, magnesium, beryllium, barium, strontium, but preferably lithium or potassium, n is the maximum valence of Met in $Met(E)_n$ and is 1 or 2 and E is as defined above for (I), except for X, leads to the tripodal cyclopentadiene derivatives (I) in which T is then preferably hydrogen, a $C_1$–$C_{20}$-carboorganic radical or a $C_1$–$C_{30}$-organosilicon radical, as specified in formula (I).

The abovementioned reactions are usually carried out in aliphatic, aromatic or preferably ether solvents; well suited solvents are tetrahydrofuran, diethyl ether, toluene. The reaction temperatures are usually in the range from −100 to 100° C., preferably in the range from −30 to 80° C.

The molar ratio $Met(E)_n$:(IIc) is generally in the range from about 10:1 to 2:1, preferably from 5:1 to 2:1 and in particular 3.5:1.

As an alternative to the above-described first synthetic route 1a), a synthetic route 1b) in which the nucleophilic opening of the oxetane derivative (IIa) plays a role has been found to be useful.

For this purpose, the above-defined oxetane derivative (IIa) is generally reacted with the above-defined reagent $Met(E)_n$ to give a compound (IIda) or (IIdb), or a mixture of (IIda) and (IIdb).

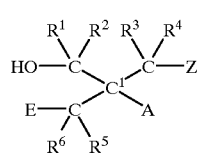

(IIda)

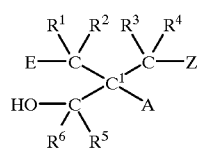

(IIdb)

If, in addition, all substituents on the central carbon atom $C^1$ in (IIda) or (IIdb) are different, stereoisomers, for example enantiomers, of (IIda) or (IIdb) generally occur. The radicals $R^1$ to $R^6$, Z, E and A in (IIda) and (IIdb) are as defined above for (I) or (IIa).

The compounds (IIda), (IIdb) are valuable intermediates since, on the one hand, they can themselves be used as ligands in metal complexes and, on the other hand, can be further varied chemically in a wide variety of ways, in particular at the OH function.

In general, the OH function in (IIda), (IIdb) is converted into a leaving group X, as defined above, using the customary methods of organic chemistry.

For this purpose, (IIda) or (IIdb) is preferably reacted with sulfonic acid derivatives such as methanesulfonyl chloride, trifluoromethanesulfonyl chloride, p-toluene sulfonyl chloride, benzenesulfonyl chloride or aqueous hydrogen bromide to give (ie.) or (ie.) which can again be in the form of regioisomers and stereoisomers. The radicals $R^1$ to $R^6$, Z, E and A are as defined above for (I) or (IIa).

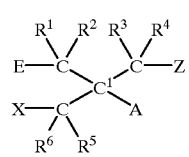

(ie.)

(ie.)

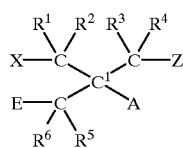

The following sequence has been found to be a very well suited variant for converting the OH function into a leaving group X.

The crude product mixture obtainable by conversion of (IIa) into (IIda), (IIdb) is generally reacted with borane complexes, for example borane-tetrahydrofuran adduct $BH_3.(OC_4H_8)$, and the OH function can subsequently be, as described above, converted into the leaving group X, for example by reacting the crude product with methanesulfonyl chloride/triethylamine. The borane can subsequently be removed using a strong Lewis base, for example an amine such as morpholine, to give (ie.) or (ie.).

The reaction of (ie.), (ie.) with $Met(E)_n$, where Met is lithium, sodium, potassium, rubidium, cesium, calcium, magnesium, beryllium, barium or strontium, preferably lithium or potassium, n is the maximum valence of Met in Met(E), and is 1 or 2 and E is as defined above for (I), preferably —P(R)(R), then leads, with replacement of X, to the tripodal cyclopentadiene derivatives (I) of the present invention, where T is preferably hydrogen, a $C_1$–$C_{20}$-carboorganic radical or a $C_1$–$C_{30}$-organosilicon radical, as specified in formula (I).

An advantage of the synthetic route Ib is that it is very suitable for introducing different radicals E into the molecule (I) and thus possibly giving stereoisomers or even pure enantiomers of (I).

Synthetic route 2 is generally selected for preparing functionalized tripodal cyclopentadiene derivatives (III).

The substituent A in (II) generally contains a group which is accessible to nucleophilic substitution. Well suited groups A are those having the structures -Y-X, where Y is a $C_1$–$C_{20}$-organic group which connects X to $C^1$ in (II) and has been defined above. Preferably, Y is a $C_1$–$C_{10}$ α,ω-alkanediyl unit such as –(C(R)(R)–$)_n$, where R are identical or different and have the meanings defined above for R, but in particular hydrogen and n is a number from 1 to 10, preferably from 1 to 3. Suitable Y are 1,2-ethanediyl —$CH_2$—$CH_2$—, 1,3-propanediyl —$CH_2$—$CH_2$—$CH_2$— and in particular methylene —$CH_2$—.

Y can also be a $C_6$–$C_{20}$-aromatic group such as p-phenylene, p-biphenylene, p-xylylene and preferably para-$CH_2$—$C_6H_4$—.

X is a leaving group as defined above, preferably bromine, methanesulfonyl $CH_3SO_2$—O—.

Compound (II) containing the -Y-X substituent defined for A is then usually reacted with the above-defined cyclopentadienyl anion equivalent $Met_nZX_m$ and the above-defined reagent $Met(E)_n$, preferably Met P(R)(R), where Met is preferably lithium or potassium and R is preferably phenyl, ethyl or m-xylyl, to give the oxetane derivative which can again, depending on the substitution in $R^1$ to $R^6$ and Y, be in the form of various isomers (IIIaa), (IIIab).

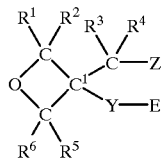

(IIIaa)

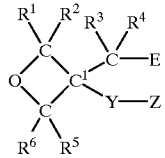

(IIIab)

To reduce the number of possible isomers, it is usual to use symmetric oxetane derivatives (II), ie., for example, those in which Y is identical to —$C(R^3)(R^4)$—; very particular preference is given to those in which Y and —$C(R^3)(R^4)$— in (II) are both methylene groups —$CH_2$—.

The compounds (IIIaa), (IIIab), which may be in the form of various isomers, are then generally reacted with the reagent $Met(E)_n$, where E is preferably —P(R)(R) where R is phenyl, ethyl, m-xylyl, and the oxetane ring is nucleophilically opened to give the compounds (IIIba), (IIIbb), (IIIbc), (IIIbd).

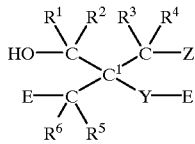

(IIIba)

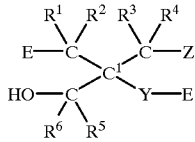

(IIIbb)

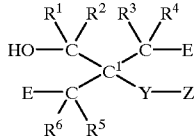

(IIIbc)

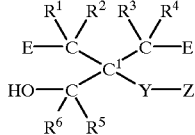

(IIIbd)

Here, in order to reduce the number of possible isomers, it is usual to meet the condition that all units —$C(R^1)(R^2)$—, —$C(R^3)(R^4)$—, —$C(R^5)(R^6)$— and —Y— are identical and, in particular, are —$CH_2$—; E is preferably then —P(R)(R).

Reaction of the OH function in IIIba, IIIbb, IIIbc or IIIbd with silylation, alkylation or acylation reagents R—X or

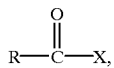

where R is as defined in (I) and X is a leaving group as defined above for (I), can then lead to the compounds (IIIca), (IIIcb), (IIIcc) or (IIIcd), where R' is RO or

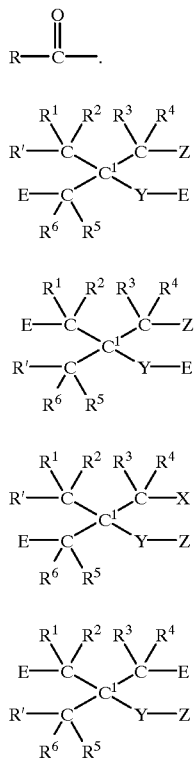

The compounds (IIIca) to (IIIcd), in particular those in which the radicals have the above-defined meaning and where $R^1$ to $R^6$ are preferably hydrogen, Y is preferably hydrogen, E is preferably —P(R)(R) and R' is preferably acyl R—C(O)—, where R is as defined above, preferably —CH$_3$, are valuable tripodal, functionalized ligands whose oxygen functionality R' can serve, for example, as anchor group for chemical or physical attachment to support material such as inorganic oxides, ie. silica gel $SiO_2$, aluminum oxide, $Al_2O_3$, or polymers such as functionalized polystyrenes, for example Merrifield Polymer.

The reaction conditions for the abovementioned reactions of synthetic route 2 are generally not critical.

The reactions are generally carried out at from −50° C. to 150° C., usually in an organic solvent, preferably alcohols, aromatic hydrocarbons and in particular tetrahydrofuran, toluene, pyridine. The compounds of the synthetic sequence II to III can either be further processed directly as crude product or else be isolated and purified first.

The following schemes 1 to 8 illustrate the variety of different synthetic routes and the variety of compounds of the type (I).

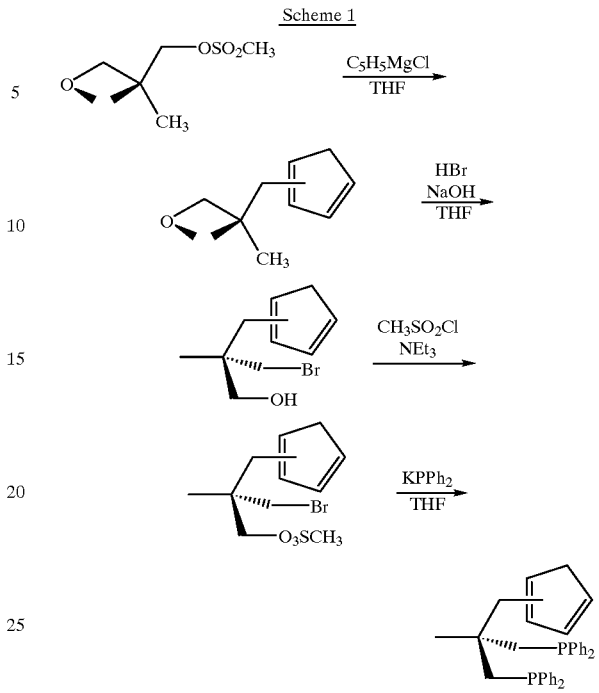

Scheme 4
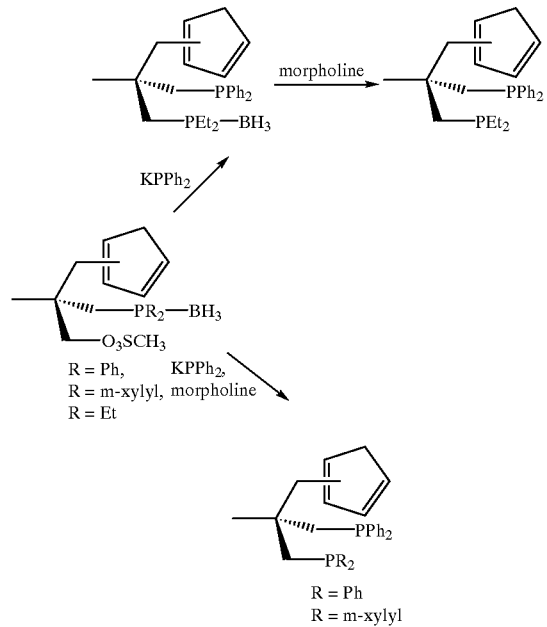
Scheme 5
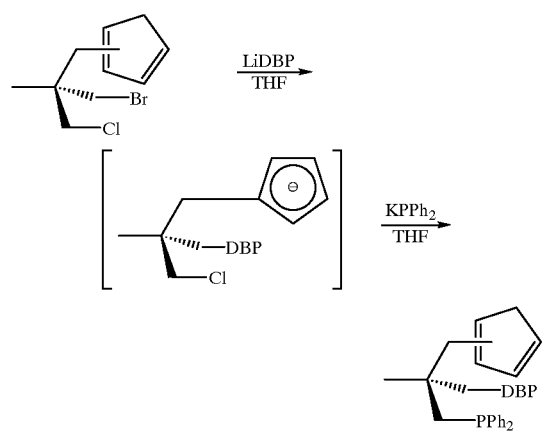
Scheme 6
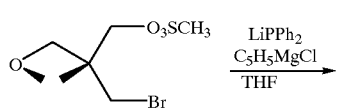
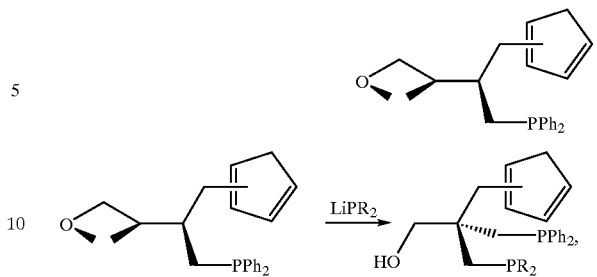
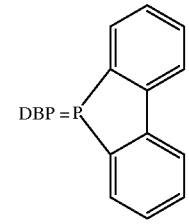
Scheme 7
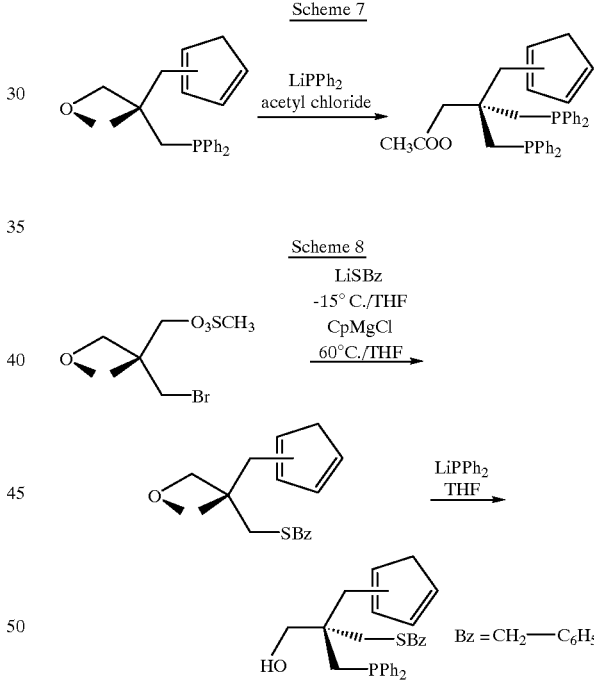
Particularly preferred compounds of the formula (I) are, for example:
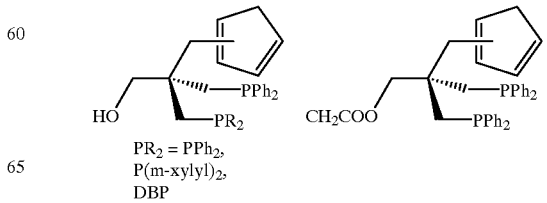

-continued

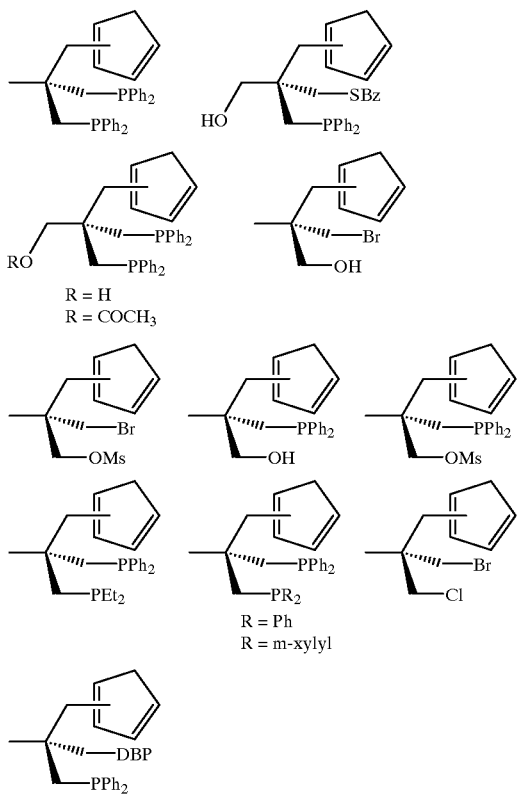

where:
Ms=$CH_3SO_2$
Ph=$C_6H_5$
Et=$C_2H_5$

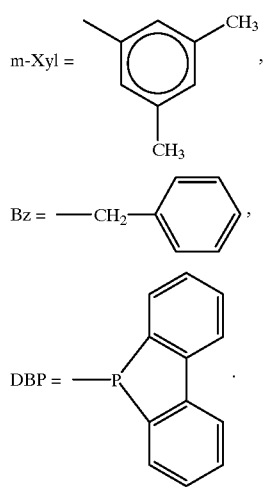

The tripodal cyclopentadiene derivatives (I) of the present invention are well suited as ligands in tripod metal complexes $L_nM(Tp)_m$ (V), where M is a transition metal or main group metal of the Periodic Table of the Elements, preferably a metal from among the transition metals of the Periodic Table and in particular Ti, Zr, Hf, Fe, Mn, Mo, Ru or Co and L is an anionic or uncharged ligand such as carbon monoxide or a $C_1$–$C_{20}$-organic radical, where the chemical nature of L is not critical and Tp are the above-defined tripodal cyclopentadiene derivatives (I), which may be singly deprotonated and are generally bound to the central metal M via the cyclopentadienyl structural unit, preferably by pi bonding and in particular by $\eta^5$ bonding. n is an integer from 0 to 7 and m is an integer from 1 to 8.

The metal complexes (V) are generally prepared by reacting a tripodal cyclopentadiene derivative (I) or a singly deprotonated tripodal cyclopentadiene derivative (I') with a metal compound bearing replaceable radicals, as described for analogous reactions with non-functionalized cyclopentadienides, for example in J. Organomet. Chem. 1989, 369, pp. 359–370.

The deprotonated tripodal cyclopentadiene derivatives (I') are usually obtained by reacting (I) with strong, generally organometallic, bases of the first, second or third main group of the Periodic Table of the Elements, for example $C_1$–$C_6$-alkyl compounds of lithium, sodium, potassium, cesium, magnesium; bases which are preferably used are n-butyllithium, alkali metal hydroxides, alkaline earth metal hydroxides, alkali metal alkoxides or alkaline earth metal alkoxides, eg. sodium methoxide, NaOEt, KOtBu; amides such as lithium diisopropylamide.

Usually, an H atom is removed from the cyclopentadienyl structural unit and is formally replaced by the metal of the organometallic base.

Such deprotonation or metallation reactions are known to those skilled in the art.

Possible replaceable radicals of the metal compound are generally those whose binding strength to the respective metal M is lower than the binding strength of the tripodal cyclopentadienyl ligand (I) or cyclopentadienide ligand (I') which displaces the replaceable radicals.

Well suited displaceable radicals are the halogens, ie. fluorine, chlorine, iodine and in particular bromine, other leaving groups X defined above, hydride, also carbon monoxide, monoolefins such as ethylene, propene, cyclohexene, cyclopentene, norbornene, diolefins such as 1,3-butadiene, cyclooctadiene, ethers such as tetrahydrofuran, diethyl ether; amines $NR_3$ such as triethylamine, phosphines $PR_3$ such as $PPh_3$, $PMe_3$, nitriles such as acetonitrile, β-diketo compounds such as acetylacetone.

Suitable metal compounds which bear replaceable radicals are, for example, all metal halides, in particular the chlorides and bromides, metal carbonyl halides, for example pentacarbonylmanganese(I) bromide $(CO)_5MnBr$, iron(II) chloride, $Fe(CO)_4Br$, metal carbonyl nitriles.

Usually, the tripodal cyclopentadiene derivative (I) or (I') is initially charged in an organic solvent, preferably tetrahydrofuran, and the metal compound, preferably a metal halide compound, is added and the mixture is stirred. The reaction temperature is generally in the range from –100 to 150° C., preferably in the range from –80 to 30° C.

The tripod complexes (V) can be chemically modified in a wide variety of ways. For example, the reaction of tripod metal halide complexes with salts of non-nucleophilic anions, for example sodium hexafluorophosphate, sodium tetrafluoroborate, lithium tetrakis(pentafluorophenyl)borate, gives the cationic metal complexes with the nonnucleophilic anions as counterions.

A further preferred modification is the replacement of the halogen ligands in the tripod metal halide complexes, for example by organic radicals R or hydrogen, where R can be as defined in (I), for example phenyl, methyl. Usually, a tripod metal halide complex is reacted at low temperature, preferably in the range from –100 to 30° C., with organometallic compounds MetR, where Met is a metal from the first, second or third main group of the Periodic Table and R is as defined in (I). Examples of MetR are phenyllithium, n-butyllithium, methyllithium or Grignard compounds such as phenylmagnesium chloride, methylmagnesium chloride.

The tripodal ligands Tp are generally bound to the metal atom M both via their cyclopentadienide structural unit and via at least one of their E donor centers. A preferred mode of bonding is for both the cyclopentadienyl structural unit ($\eta^5$) and also two donor centers E, where E is preferably —P(R)(R), as defined above, to be bonded to the metal atom M (tripod geometry).

The ligands (I) of the present invention can be advantageously used for the preparation of metal complexes. The metal complexes can be used as mediators or as catalysts or as constituents of catalysts or mediators for stereoselective or regioselective reactions in organic chemistry, stoichiometric or catalytic carbon-carbon bond formation or hydrogenation, for example the hydrogenation of C=C or C=O double bonds.

Furthermore, the metal complexes themselves are suitable as catalysts or as constituents of catalytically active mixtures, in particular for the polymerization of hydrocarbon monomers or functionalized monomers. Examples which may be mentioned are C=C monomers such as alk-1-enes, ie. ethene, propene, 1-butene, 1-hexene and 1-octene, or acrylic acid or its derivatives such as methyl acrylate, ethyl acrylate and n-butylacrylate or styrene and its derivatives.

EXAMPLES

General

All work was carried out under dried argon in Schlenk vessels. The following chemicals were prepared as described in the literature:

3-methanesulfonoxymethyl-3-methyl-3-oxetane (1) as described by J. Cheymol, P. Chabrier, J. Seyden-Penne, A. Habert-Somny, T. Strazalko, *Bull. Soc. Chim. Fr.* 1965, 694;

3-bromo-2-chloromethyl-1-propyl trifluoromethanesulfonate (11) as described by H. Heidel, G. Huttner, G. Helmchen, *Z. Naturforsch., Part B* 1993, 48, 1681;

$(CO)_5MnBr$ as described by W. P. Fehlhammer, W. A. Herrmann, K. Öfele in Brauer, *Handbuch der Präparativen Anorganischen Chemie*, Vol. 3, Ferdinand Enke Verlag, Stuttgart 1978;

1,1-bis(diphenylphosphinomethyl)-1-cyclopentadienylmethyl-ethane (5a), 1-cyclopentadienyl-2-(di-m-xylylphosphinomethyl)-2-(diphenylphosphinomethyl)propane (5b) and 1-cyclopentadienyl-2-diethylphosphinomethyl-2-diphenylphosphino-methylpropane (5c) were prepared as described in Examples 5, 15, 17;

diphenylphosphine and di-m-xylylphosphine as described by R. E. Ireland, D. M. Walba, *Org. Synth.* 1977, 56, 47;

5-H-dibenzophosphole as described by J. Cornforth, R. H. Cornforth, R. T. Grey, *J. Chem. Soc. Perkin Trans. I.* 1982, 2289 or H. Braye, I. Caplier, R. Saussez, *Tetrahedron* 1971, 27, 5523;

cyclopentadienylmagnesium chloride as described by J. R. Stille, R. H. Grubbs, *J. Org. Chem.* 1989, 54, 434;

$Mo(CH_3CN)_3(CO)_3$ as described by D. B. Tate, W. R. Knipple, J. M. Augl, *Inorg. Chem.* 1962, 7, 433;

$(PPh_3)_2FeCl_2$ as described by L. H. Pegnolet, D. Forster, W. d. W. Horrocks, Inorg. Chem., 1968, 7, p. 828.

Analysis:

UV/VIS spectrophotometer Lambda 9 from Perkin Elmer, $CH_2Cl_2$ solutions in Hellma 110 suprasil cuvettes (0.2 cm path length)

Cyclovoltametry: measurement conditions: $10^{-3}$ M solution in 0.1 M $n-Bu_4NPF_6/CH_3CN$ solution in a Metrohm cell, voltage advance 200 mV/sec, potential in volts relative to a saturated calomel electrode on a glassy carbon electrode at 25° C., potentiostat/galvanostat Model 273 from EG & G Princeton Applied Research.

ESR spectra were recorded using a Bruker ESP 300E spectrometer (X band, external standard DPPH (diphenylpicrylhydrazyl)).

Photochemical reactions: carried out in a coolable Duran glass 50 apparatus using a Hanau TQ 150 high-pressure mercury vapor lamp.

NMR& Bruker AC-200 (298 K) ($^1$H: 200 MHz; $^{13}$C: 50 MHz). Internal standard by means of $CDCl_3$ solvent ($\delta$=7.27 for $^1$H, 77.0 for $^{13}$C) relative to external TMS. $^{31}$P: 81 MHz, external $H_3PO_4$ standard (85%). The $^{13}$C— and $^{31}$P-NMR spectra were recorded with $^1$H decoupling. Abbreviations: bs (broad signal), d (doublet), dd (doublet of doublets), t (triplet), pt (pseudotriplet), m (multiplet); singlets are not denoted by a separate designation. All measurements were carried out in $CDCl_3$ as solvent.

MS: Finnigan MAT 8230 with data system SS 300, EI (70 eV), FAB (matrix: 4-nitrobenzyl alcohol, triethanolamine); the m/e values are based on the most abundant isotrope in each case.

Elemental analyses: microanalytical laboratory of the Organisch-Chemischen Institut of the University of Heidelberg.

The numbered structural formulae are shown after the examples.

Preparations:

Example 1

3-Cyclopentadienylmethyl-3-methyloxetane (2)

In a 500 ml three-neck flask fitted with dropping funnel, reflux condenser and protective gas connection, 70.0 g (230 mmol) of CpMgCl*2THF were dissolved in 200 ml of THF with exclusion of air and moisture. The dark solution was heated to 60° C. and, at this temperature, a solution of 28.8 g (192 mmol) of 1 in 100 ml of THF was added dropwise over a period of 2 hours. The solution was subsequently refluxed for 2 hours. After cooling, it was hydrolyzed with 200 ml of 10% strength ammonium chloride solution. The aqueous phase was extracted three times with 50 ml of diethyl ether and the combined organic phases were washed with saturated sodium chloride solution until neutral. After drying over sodium sulfate, the yellow oil was fractionally distilled under reduced pressure. 2 goes over at 63–66° C (2.7 mbar) as a colorless to slightly yellowish oil, yield: 18.1 g (63%). MS (EI); m/e (%) [frag.]: 150 (10%) [M$^+$], 105 (100%) [M$^+$—CH$_2$O—CH$_3$], 79 (70%) [HC$_5$H$_4$CH$_2$$^+$). $C_{10}H_{14}O$ (150.22): calc.: C 79.97, H 9.39, O 10.64; found: C 79.22, H 9.44.

Example 2

2-Bromomethyl-2-cyclopentadienylmethyl-1-propanol (3)

In a 500 ml Schlenk tube (8 cm diameter), 4.5 g (30 mmol) of 2 were dissolved in 150 ml of THF and cooled to −70° C. An aqueous solution of HBr was added dropwise over a period of 5 minutes and the solution was stirred further for 2 hours at this temperature. After removing the cooling bath, the solution thawed to −15° C. over a period of 1.5 hours. The reaction solution was hydrolyzed at this temperature by addition of 40 ml of 10% strength sodium hydroxide solution and was stirred for 1 hour without cooling. During this time, the solution came to room temperature. The aqueous phase was separated off and shaken three times with 30 ml of diethyl ether. The combined organic phases were subsequently washed with saturated sodium chloride solution and dried over sodium sulfate. Removal of the solvent gave a yellow oil. The crude product obtained in this way (6.97 g) can be reacted further without further purification. To characterize the material, part of the crude product was flash-chromatographed on a silica gel column (4*25 cm; eluant: PE/THF in a ratio of 9:1; $R_F$=0.18). Evaporation of the product fractions gave 3 as a colorless oil.

MS (EI); m/e (%) [frag.]: 231 (10 %) [M$^+$], 79 (100 %) [HC$_5$H$_4$CH$_2$$^+$]. C$_{10}$H$_{15}$BrO (231.132): calc. C 51.97, H 6.54, Br 34.57, O 6.92; found. C 52.21, H 6.58, Br 34.55.

Example 3

2-Bromomethyl-2-cyclopentadienylmethyl-1-propyl methanesulfonate (4)

In a 200 ml Schlenk tube fitted with a septum, 6.97 g of crude product 3 and 4.35 ml (45 mmol) of triethylamine were dissolved in 100 ml of methylene chloride. At 0° C., 2.37 ml (31 mmol) of methanesulfonyl chloride were injected over a period of 2 minutes. After half the methanesulfonyl chloride had been added, a colorless precipitate formed. The suspension was held at this temperature for another half hour and was then stirred for 2 hours at room temperature. The reaction solution was subsequently hydrolyzed with 20 ml of water. The phases were separated and the aqueous phase was extracted three times with 20 ml of methylene chloride. The combined organic phases were washed with sodium chloride solution until neutral and dried over sodium sulfate. Removal of the solvent in an oil pump vacuum gave a slightly brownish oil which was dissolved in methylene chloride and absorbed on kieselguhr. This was followed by flash chromatography on a silical gel column (4*25 cm; PE/THF in a ratio of 8:2; $R_F$=0.42). Evaporation of the product fractions in an oil pump vacuum gave 5.9 g (66%) of 4 as a colorless oil.

MS (EI); m/e (%) [frag.]: 308 (7%) [M$^+$–1], 133 (30%) [M$^+$-HBr-OMs], 79 (100%) [HC$_5$H$_4$CH$_2$$^+$]. C$_{11}$H$_{17}$BrO$_3$S (309.218): calc. C 42.73, H 5.54, Br 25.840 15.52, S 10.37; found. C 42.62, H 5.58.

Example 4

Method of preparing potassium diphenylphosphide

One equivalent of KOtBu was added at 0° C. to an approximately 0.3 M solution of diphenylphosphine in THF and the bright red solution formed was stirred further for at least half an hour.

Example 5

1,1-Bis(diphenylphosphinomethyl)-1-cyclopentadienyl-methyl-ethane (5a)

Method A: 3 equivalents of a potassium diphenylphosphide solution were placed in a 500 ml three-neck flask fitted with septum, reflux condenser and inert gas connection and a solution of 6.18 g (20 mmol) of 4 in 70 ml of THF was added over a period of 2 minutes. The solution was refluxed for 3 hours and, after cooling, the solvent was removed in an oil pump vacuum. The residue was taken up in 70 ml of diethyl ether and hydrolyzed with 30 ml of water. The aqueous phase was separated off and extracted three times with 30 ml of diethyl ether. The combined organic phases were washed with sodium chloride solution until neutral and dried over sodium sulfate. The solvent was taken off in an oil pump vacuum, the resulting viscous, colorless residue was dissolved in methylene chloride and absorbed on kieselguhr. Flash chromatography on a silica gel column (12*8 cm; eluant: PE/diethyl ether in a ratio of 9.75:0.25; $R_F$=0.32) and removal of the solvent gave 5a as a colorless oil, yield: 6.0 g (60%).

Example 6

General method of preparing lithium dibenzophospholide, lithium diarylphosphides and lithium dialkylphosphides One equivalent of n-BuLi solution in hexane (about 2.3 M) was added dropwise at 0° C. to an approximately 0.3 M solution of the diarylphosphine or dialkylphosphine in THF over a period of about 5 minutes. The solution was subsequently stirred further for at least half an hour. The red solutions prepared in this way were used directly for syntheses.

Example 7

2-cyclopentadienylmethyl-2-diphenylphosphinomethyl-1-propanol (6)

In a 250 ml three-neck flask fitted with reflux condenser, septum and inert gas connection, 1.4 g (13.4 mmol) of 2 were dissolved in 50 ml of THF and deprotonated at 0° C. by injecting in 5.6 ml (13.4 mmol) of n-BuLi solution. The mixture was stirred further for half an hour. Via a capillary hose, 1.5 equivalents of a lithium diphenylphosphide solution were added thereto at room temperature over a period of half an hour. The reaction solution was subsequently refluxed for 2 hours. The reaction mixture was substantially freed of solvent in an oil pump vacuum and the residue was taken up in 50 ml of diethyl ether. The mixture was hydrolyzed by addition of 20 ml of water and was stirred further for 10 minutes. The organic phase was separated off and the aqueous phase was extracted twice with 30 ml of diethyl ether. The combined ether phases were washed with sodium chloride solution until neutral and dried over sodium sulfate. The remaining colorless oil was dissolved in methylene chloride and absorbed on kieselguhr. This was followed by flash chromatography on silica gel (20*4 cm; eluant: PE/THF in a ratio of 8.5:1.5; $R_F$=0.30). Removal of the solvent gave 6 as a colorless, viscous oil; yield 3.37 g (75%).

MS (EI); m/e (%) [frag.]: 337 (100%) [M$^+$+1], 183 (24%) [PPh$_2$$^+$–2H]. C$_{22}$H$_{25}$OP (336.413): calc. C 78.54, H 7.49, O 4.76, P 9.21; found. C 77.94, H 7.42.

Example 8

2-Cyclopentadienylmethyl-2-diphenylphosphinomethylborane-1-propanol (7a)

The reaction and work-up to give the crude product was carried out by a method similar to Example 7 using 1.55 g (10.32 mmol) of 2 in 50 ml of THF and 1.2 equivalents of a diphenylphosphide solution.

After work-up of the reaction solution, the crud product 6 was dissolved in 20 ml of THF and cooled to 0° C. in an ice bath. 14.9 ml of a IM solution of BH$_3$ in THF were injected over a period of half a minute. The mixture was stirred further for half an hour at this temperature and the solvent was then removed in an oil pump vacuum. The colorless oil which remained was dissolved in methylene chloride and absorbed on kieselguhr. This was followed by flash chromatography on silica gel (20*4 cm; eluant: PE/THF in a ratio of 7.35:2.65, $R_F$=0.30). Removal of the solvent gave 7a as a colorless, viscous oil, yield: 2.42 g (67%).

MS (FAB); m/e (%) [frag.]: 349 (100%) [M$^+$–1). C$_{22}$H$_{28}$BOP (350.257): calc. C 75.44, H 8.06, B 3.09, O 4.57, O 4.57, P 8.84; found. C 74.97, H 8.10, P 8.57.

Example 9

2-Cyclopentadienylmethyl-2-di-m-xylylphosphinomethylborane-1-propanol (7b)

The preparation was carried out using a method similar to that for 7a. 2.28 g (15.2 mmol) of 2 were deprotonated with 7 ml (15.2 mmol) of n-BuLi solution and reacted with 1.2 equivalents of lithium di-m-xylylphosphide to give the crude product 7b which was reacted with 21.9 ml of a 1M solution of BH$_3$ in THF. After flash chromatography on silica gel (20*4 cm; eluant: PE/THF in a ratio of 8.5:1.5; R$_F$=0.28) 4.9 g (80%) of 7b were obtained as a colorless, viscous oil.

MS (FAB); m/e (%) [frag.]: 405 (45%) [M$^+$−], 241 (100%) [P(m-Xyl)$_2$$^+$]. C$_{26}$H$_{36}$OPB (406.364): calc. C 76.84, H 8.87, B 2.71, O 3.94, P 7.64; found. C 75.47, H 9.19.

Example 10
2-Cyclopentadienylmethyl-2-diethylphosphinomethylborane-1-propanol (7c)

The preparation was carried out using a method similar to that for 7a. 1.5 g (10 nmmol) of 2 were deprotonated with 4 ml (10 mmol) of n-BuLi solution and reacted with 1.2 equivalents of lithium diethylphosphide to give the crude product 7c which was reacted with 15.6 ml of a 1M solution of BH$_3$ in THF. After flash chromatography on silica gel (20*4 cm; eluant: PEgTHF in a ratio of 7.5:2.5; R$_F$=0.39) 2.0 g (78%) of 7c were obtained as a colorless, viscous oil.

MS (El); m/e (%) [frag.]: 254 (38%) [M$^+$], 240 (25%) [M$^+$-BH$_3$], 225 (15%) [M$^+$-C$_2$H$_5$], 209 (16%) [M$^+$-CH$_2$OH-BH$_3$], 117 (60%) [M$^+$-BH$_3$—CH$_2$PEt$_2$]. C$_{14}$H$_{28}$BOP (254.168): calc. C 66.16, H 11.10, B 4.25, O 6.30, P 12.19; found. C 66.08, H 11.04, P 12.17.

Example 11
2-Cyclopentadienylmethyl-2-diphenylphosphinomethyl-borane-1-propyl methane sulfonate (8a)

In a 250 ml three-neck flask fitted with inert gas connection, 2.4 g (6.86 mmol) of 7a were dissolved in 50 ml of methylene chloride and admixed with 1.4 ml (10.3 mmol) of triethylamine. At 0° C., 0.7 ml (8.91 mmol) of methanesulfonyl chloride was injected and the reaction solution was stirred for 16 hours at room temperature. After hydrolysis with 20 ml of water, the organic phase was separated off and the aqueous phase was extracted three times with 50 ml each time of methylene chloride. The combined organic phases were subsequently washed with saturated sodium chloride solution until neutral and dried over sodium sulfate. Evaporation of the solution in an oil pump vacuum gave a brownish oil which was again dissolved in methylene chloride and absorbed on kieselguhr. After flash chromatography on silica gel (20*4 cm; eluant: PE/THF in a ratio of 7:3; R$_F$=0.30), 8a was obtained in the form of a colorless solid, yield: 2.2 g (75%).

MS (EI); m/e (%) [frag.]: 428 (10%) [M$^+$], 414 (50%) [M$^+$-BH$_3$], 335 (35%) [M$^+$-BH$_3$—SO$_2$CH$_3$], 183 (100%) [PPh$_2$$^+$-2H]. C$_{23}$H$_{30}$BO$_3$PS (428.339): calc. C 64.49, H 7.06, B 2.52, O 11.21, P 7.24, S 7.48; found. C 64.52, H 7.21, P 7.98.

Example 12
2-Cyclopentadienylmethyl-2-di-m-xylylphosphinomethyl-borane-1-propyl methylsulfonate (8b)

The preparation was carried out using a method similar to that for 8a. 4.46 g (11.46 mmol) of 7b, 2.4 ml (17.35 mmol) of triethylamine and 1.2 ml (14.9 mmol) of methanesulfonyl chloride in 70 ml of methylene chloride gave, after flash chromatography on silica gel (20*4 cm; eluant: PE/THF in a ratio of 8:2; R$_F$=0.31), 8b as a colorless solid, yield: 3.7 g (67%).

MS (FAB); m/e (%) [frag.]: 484 (3%) [M$^+$], 470 (40%) [M$^+$-BH$_3$], 241 (100%) 1P(m-Xyl)$_2$$^+$]. C$_{27}$H$_{38}$BOPS (484.447): calc. C 66.94, H 7.91, B 2.23, O 9.91, P 6.39, S 6.62; found. C 64.02, H 7.60.

Example 13
2-Cyclopentadienylmethyl-2-diethylphosphinomethyl-borane-1-propyl methanesulfonate (8c)

The preparation was carried out using a method similar to that for 8a. 3.42 g (13.4 mmol) of 7c, 3 ml (21.4 mmol) of triethylamine and 1.3 ml (16 mmol) of methanesulfonyl chloride in 70 ml of methylene chloride gave, after flash chromatography on silica gel (25*4 cm; eluant: PE/THF in a ratio of 7.5:2.5; R$_F$=0.38), 8c as a colorless solid, yield: 3.6 g (82%).

MS (EI); m/e (%) [frag.]: 332 (11%) [M$^+$], 318 (50%) [M$^+$-BH$_3$], 253 (80%) [M$^+$-SO$_2$CH$_3$]; 223 (65%) [M$^+$-CH$_2$OSO$_2$CH$_3$], 79 (75%) [HC$_5$H$_4$CH$_2$$^+$ and SO$_2$CH$_3$$^+$]. C$_{15}$H$_{30}$BO$_3$PS (332.261): calc. C 54.19, H 9.10, B 3.31, O 14.45, P 9.32, S 9.63; found. C 53.42, H 8.92.

Example 14
2-Cyclopentadienylmethyl-2-diphenylphosphino-methyl-1-propyl methanesulfonate (9)

The reaction and work-up to give the crude product were carried out by a method similar to that for 8a using 2.89 g (8.26 mmol) of 7a, 1.7 ml (12.39 mmol) of triethylamine and 0.85 ml (10.74 mmol) of methanesulfonyl chloride in 50 ml of methylene chloride.

The worked-up crude product 8a was dissolved in 2 ml of morpholine and stirred for 15 minutes at 70° C. After removing the morpholine in an oil pump vacuum, the oil was taken up in methylene chloride and absorbed on kieselguhr. The product was subsequently purified by flash chromatography on silica gel (20*4 cm; eluant: PE/THF in a ratio of 8:2; R$_F$=0.27). Evaporation of the product fractions under reduced pressure gave 9 in the form of a colorless oil, yield: 2.5 g (73%).

MS (EI); m/e (%) [frag.]: 414 (60%) [M$^+$], 335 (50%) [M$^+$-SO$_2$CH$_3$], 199 (55%) [CH$_2$PPh$_2$$^+$], 183 (100%) [PPh$_2$$^+$-2H]. C$_{23}$H$_{27}$O$_3$PS (414.507): calc. C 66.64, H 6.57, O 11.59, P 7.48, S 7.72; found. C 66.23, H 6.74.

Example 15
1-Cyclopentadienyl-2-(di-m-xylylphosphinomethyl)-2-(diphenylphosphinomethyl)propane (5b)

3.5 equivalents of potassium diphenylphosphide solution were placed in a 250 ml three-neck flask fitted with septum, reflux condenser and inert gas connection and a solution of 2.62 g (5.42 mmol) of 9 in 50 ml of THF was added over a period of 2 minutes. The reaction mixture was subsequently stirred for 16 hours at room temperature. A colorless precipitate was formed during this time. The reaction mixture was substantially freed of solvent in an oil pump vacuum and the residue was taken up in 50 ml of diethyl ether. Hydrolysis was carried out by adding 20 ml of water and the mixture was stirred for 10 minutes. The organic phase was separated off and the aqueous phase was extracted twice with 30 ml of diethyl ether. The combined ether phases were washed with sodium chloride solution until neutral and dried over sodium sulfate. The colorless oil which remained was taken up in 5 ml of morpholine and heated at 70° C. on an oil bath for half an hour. The morpholine was taken off in an oil pump vacuum, the residue was dissolved in methylene chloride and absorbed on kieselguhr. This was followed by flash chromatography on silica gel (20*4 cm; eluant: PE/Diethylether in a ratio of 9.75:0.25; R$_F$=0.31). This gave 1.42 g (47%) of Sb as colorless, viscous oil.

MS (EI); m/e (%) [frag.]: 560 (70%) [M$^+$], 483 (100%) [M$^+$-C$_6$H$_5$], 375 (98) [M$^+$-PPh$_2$], 319 (50%) [M$^+$-P(m-Xyl)$_2$], 241 (100%) [P(m-Xyl)$_2$$^+$], 183 (85%) [PPh$_2$$^+$-2H]. C$_{38}$H$_{42}$P$_2$ (560.699): calc. C 81.40, H 7.55, P 11.05; found. C 80.43, H 7.63.

Example 16
1-Cyclopentadienyl-2-diethylphosphinomethylborane-2-diphenylphosphinomethyl-propane (10)

The reaction and work-up to give the crude product 10 were carried out using a method similar to that for 5b, without the latter being reacted further in morpholine. The crude product from 2.77 g (8.3 mmol) of 8c and 3 equivalents of potassium diphenylphosphide was purified by flash chromatography on silica gel (25*4 cm; eluant: PE/diethyl ether in a ratio of 9.5:0.5; $R_F$=0.35). Evaporation of the product fractions in an oil pump vacuum gave 1.69 g (48%) 10 as a colorless, viscous oil.

MS (EI); m/e (%) [frag.]: 422 (9%) [M$^+$], 408 (16%) [M$^+$-BH$_3$], 379 (100%) [M$^+$-BH$_3$-C$_2$H$_5$], 183 (22%) [PPh$_2^+$-2H]. C$_{26}$H$_{37}$BP$_2$ (422.346).

Example 17
1-Cyclopentadienyl-2-diethylphosphinomethyl-2-diphenylphosphinomethyl-propane (5c)

1.69 g (4 mmol) of 10 were dissolved in 5 ml of morpholine and stirred at 80° C. for 2 hours. After removing the unreacted morpholine in an oil pump vacuum, the resulting colorless oil was taken up in methylene chloride, absorbed on kieselguhr and purified by column chromatography on silica gel (25*3 cm; eluant: PE/diethyl ether in a ratio of 9:1; $R_F$=0.55). Removal of the solvent gave 5c in the form of a colorless oil, yield: 1.35 g (84%).

MS (EI); m/e (%) [frag.]: 408 (6%) [M$^+$], 379 (100%) [M$^+$-CH$_2$CH$_3$], 331 (4%) [M$^+$-C$_6$H$_5$], 183 (19%) [PPh$_2^+$-2H]. C$_{26}$H$_{34}$P$_2$ (408.503): calc. C 76.45, H 8.39, P 15.16; found. C 75.36, H 8.48, P 14.94.

Example 18
2-Bromomethyl-2-chloromethyl-1-cyclopentadienyl-propane (12)

In a 250 ml three-neck flask fitted with inert gas connection and dropping funnel, 8.63 g (28.39 mmol) of CpMgCl*2.5THF were dissolved in 100 ml of THF. A solution of 2.60 g (7.80 mmol) of 11 in 50 ml of THF was added dropwise from the dropping funnel over a period of 1 hour. The brown reaction mixture was subsequently stirred for 16 hours at room temperature. It was hydrolyzed by addition of 50 ml of 10% strength ammonium chloride solution and stirring for 10 minutes. The aqueous phase was separated off and extracted three times with 30 ml of diethyl ether. The combined organic phases were dried over sodium sulfate and the solvent was removed in an oil pump vacuum. The resulting yellow oil was taken up in methylene chloride and absorbed on kieselguhr. This was followed by flash chromatography on kieselguhr (10*4 cm; eluant: PE, $R_F$=0.35). Removal of the solvent in an oil pump vacuum gave 1.70 g (87%) of 12 in the form of a colorless to slightly yellowish oil.

MS (EI); m/e (%) [frag.]: 250 (18%)[M$^{+1}$, 79 (100%) [HC$_5$H$_4$CH$_2^+$]. C$_{10}$H$_{15}$BrCl (249.578): calc. C 48.13, H 5.64, Br 32.01, Cl 14.22; found. C 48.46, H 5.70

Example 19
1-Cyclopentadienyl-2-(5-dibenzophospholylmethyl)-2-(diphenylphosphinomethyl)propane (5d)

In a 250 ml Schlenk tube fitted with a septum, 1.58 g (6.31 mmol) of 12 were dissolved in 50 ml of THF, deprotonated at 0° C. by addition of 2.75 ml of n-BuLi solution and stirred further for half an hour. Via a capillary hose, one equivalent of a lithium dibenzophospholide solution was added dropwise at 0° C. over a period of half an hour. The yellow-orange reaction mixture was stirred for another 2 hours at this temperature and subsequently evaporated to about 30 ml in an oil pump vacuum. At room temperature, the reaction solution was then added to 3.5 equivalents of a potassium diphenylphosphide solution over a period of 1 minute and the mixture was stirred for 16 hours at room temperature. The solvent was subsequently substantially removed in an oil pump vacuum and the residue was taken up in 50 ml of diethyl ether. Hydrolysis was carried out by adding 20 ml of water and stirring for 10 minutes. The organic phase was separated off and the aqueous phase was extracted twice with 30 ml of diethyl ether. The combined ether phases were washed with sodium chloride solution until neutral and dried over sodium sulfate. The solvent was removed in an oil pump vacuum, the residue was dissolved in methylene chloride and absorbed on kieselguhr. This was followed by flash chromatography on silica gel (20*4 cm; eluant: PE/diethyl ether in a ratio of 9.75:0.25; $R_F$=0.31). This gave 0.7 g (22%) of 5d as a colorless, viscous oil.

MS (EI); m/e (%) [frag.]: 502 (25%) [M$^+$-H], 319 (60%) [M$^+$-H-DBP], 183 (100%) [DBP$^+$). C$_{34}$H$_{32}$P$_2$ (502.574): calc. C 81.26, H 6.42, P 12.32; found. C 82.79, H 7.17.

Example 20
Carbonyl[2,2-bis(diphenylphosphinomethyl)-η$^5$-cyclopentadienylpropyl]manganese(I) (13)

In a 100 ml Schlenk tube, 0.45 g (0.9 mmol) of 5a was dissolved in 30 ml of THF, deprotonated with 0.4 ml of 2.3 molar n-BuLi solution and stirred further for half an hour. 0.25 g (0.91 mmol) of BrMn(CO)$_5$ was added at room temperature to the above solution. The orange reaction mixture was stirred for 1 hour at this temperature and the solution was refluxed for a further 3 hours. The solvent was removed completely in an oil pump vacuum, the residue was taken up in 30 ml of diethyl ether and filtered through 2 cm of kieselguhr in a G3 reversible frit. The filtrate was again evaporated in an oil pump vacuum. The resulting orange residue was washed three times with 10 ml of petroleum ether and taken up in 100 ml of THF. The solution was then irradiated at 50° C. After six hours, an IR spectrum of the reaction solution showed only one carbonyl band at v=1829 cm$^{-1}$. The solvent was removed in an oil pump vacuum and the residue was absorbed on silica gel. This was followed by flash chromatography on silica gel (14*2 cm; eluant: PE/THF in a ratio of 8.5:1.5; $R_F$=0.47). The product runs as strongly colored orange bands. 132 mg (25%) of 13 were obtained in the form of an orange powder. Orange crystals which were suitable for X-ray structural analysis were obtained by gas-phase diffusion of petroleum ether into a toluene solution of 13 at 3° C. over a period of 24 hours.

1H-NMR: δ=1.55 (bs, 3H, CH$_3$); 1.88 (2H, CH$_2$Cp); 2.13 (m, 1H, CH$_{2a}$P, 2J$_{HH}$=15.1 Hz, 2J$_{HP}$=5 Hz, 4J$_{HP}$=4.1 Hz); 2.40 (m, 1H, CH$_{2b}$P, 2J$_{HH}$=15.4 Hz, 2J$_{HP}$=5 Hz, 4J$_{HP}$=4.1 Hz); 3.60 (bs, 2H, Cp); 4.43 (bs, 2H, Cp); 6.71–7.63 (m, 20H, aromat. H). 13C{1H}-NMR: δ=33.8 (t, CH$_3$, 3J$_{CP}$=11.3 Hz); 35.0 (pt, CH$_2$P, 1J$_{CP}$=10.3 Hz, 3J$_{CP}$=10.3 Hz); 38.8 (CH$_2$Cp); 45.2 (bs, C$_q$); 75.1, 83.4 (C$_{ipso}$), 91.2 (Cp); 127.0–145.9 (m, aromat. C). 31P{1H}-NMR: δ=86.3. IR (THF): v$_{CO}$=1829 cm−1. MS (FAB); m/e (%) [frag.]: 586 (30%) [M+]; 558 (100%) [M+-CO]. C$_{35}$H$_{33}$MnOP$_2$ (586.532): calc. C 71.67, H 5.67, Mn 9.37, O 2.73, P 9.21; found. C 71.82, H 6.11.

Example 21
General method of preparing the deprotonated ligands 5a–c:

One equivalent of n-BuLi solution in hexane (about 2.3 M) was injected at 0° C. into an approximately 0.05 M solution of the ligands 5a–c in THF and the resulting pale yellow solutions were stirred further for at least half an hour.

Example 22
2,2-Bis(diphenylphosphinomethyl)-θ$^5$-cyclopentadienylpropyl- iron(II) chloride (14c)

In a 100 ml Schlenk tube, 0.13 g (1.02 mmol) of $FeCl_2$ was suspended in 30 ml of THF and stirred for 15 minutes at room temperature. One equivalent of a solution of deprotonated 5a was then slowly added dropwise over a period of 5 minutes by means of a syringe. The initially red-violet color of the suspension changed to a deep blue during this addition.

After stirring for two hours at room temperature, the reaction mixture was evaporated to dryness in an oil pump vacuum. The residue was filtered through 10 cm of silica gel using a solvent mixture of $Et_2O/CH_2Cl_2$ in a ratio of 4:1. Removal of the solvent gave 480 mg (81%) of 14c in the form of a blue powder. Gas-phase diffusion of $Et_2O$ into a concentrated solution of the complex in $CH_2Cl_2$ enables deep blue single crystals to be obtained after 5 days.

1H-NMR: 1.18 (s, 2H, $CH_2Cp$); 1.46 (bs, 3H, $CH_3$); 2.25 (m, 2H, $CH_{2a}P$, $2J_{HH}$=6.9 Hz, $2J_{HP}$=$4J_{HP}$=5 Hz); 2.54 (m, 2H, $CH_{2b}P$, $2J_{HH}$=6.9 Hz, $2J_{HP}$=$4J_{HP}$=5 Hz); 3.92 (bs, 2H, Cp); 4.95 (t, 2H, Cp, $3J_{HP}$=1.9 Hz); 6.62–8.25 (m, 20H, aromat. H). 13C{1H}-NMR: 38.8 (t, $CH_3$, $3J_{CP}$=6.9 Hz); 34.5 (t, $CH_2P$, $1J_{CP}$=10.2 Hz); 37.1 (s, $CH_2Cp$); 45.4 (s, $C_q$); 59.7 ($C_{ipso}$), 83.6, 89.1 (3s, Cp); 127.5–144.9 (m, aromat. C). 31P{1H}-NMR: 46.1 (bs). WV/VIS ($CH_2Cl_2$): 402 sh (600); 530 sh (706); 583 (848). MS (FAB): m/e (%) [frag.]: 610 (100%) [M+]; 575 (25%) [M+-Cl]; 504 (25%) [M+-FeCl]. CV ($CH_3CN$): $E_{1/2}$=–176 mV; DE=74 UV. $C_{34}H_{33}P_2FeCl$ (594.89): calc. C 68.63, H 5.55, P 10.43, Cl 5.97, Fe 9.42; found. C 67.96, H 5.93.

Example 23
2-Diphenylphosphinomethyl-2-di(m-xylyl)phosphinomethyl-$\eta^5$-cyclopentadienylpropyl-iron(II) chloride (14d)

This compound was prepared from $FeCl_2$ using a method similar to that for 14c: 0.09 g (0.71 mmol) of iron(II) chloride suspended in 30 ml of THF and one equivalent of a solution of deprotonated 5b gave, after removal of the solvent, the crude product 14d. The crude product was filtered through 6 cm of silica gel using a solvent mixture of $Et_2O/CH_2Cl_2$ in a ratio of 7:1. Taking off the solvent in an oil pump vacuum gave 300 mg (60%) of 14d as a blue powder. Gas-phase diffusion of PE into a concentrated toluene solution of the complex covered by a layer of $Et_2O$ enabled deep blue single crystals to be obtained after 7 days.

1H-NMR: 1.15 (bs, 2H, $CH_2CP$); 1.47 (bs, 3H, $CH_3$); 1.92 (s, 6H, xylyl-$CH_3$); 2.20–2.59 (2m, 4H, $CH_{2a,b}PPh_2$, $CH_{2a,b}P(m-Xyl)_2$); 2.40 (s, 6H, xylyl-$CH_3$); 3.92 (bs, 2H, Cp); 4.93 (bs, 2H, Cp); 6.39–8.26 (m, 16H, aromat. H). 31P{1H}-NMR (223 K): 47.9 (bs). MS (FAB); m/e (%) [frag.]: 650 (100%) [M+]; 615 (30%) [M+-Cl]. CV ($CH_3CN$): $E_{1/2}$=–212 mV; DE=67 mV. $C_{38}H_{41}P_2FeCl$ (650.997): calc. C 70.14, H 6.36, P 9.53, Cl 5.37, Fe 8.60; found. C 70.32, H 6.85.

Example 24
2-Diethylphosphinomethyl-2-diphenylphosphinomethyl-$\eta^5$-cyclopentadienylpropyl-iron(II) chloride (14e)

This compound was prepared from $FeCl_2$ using a method similar to that for 14c: 0.07 g (0.58 mmol) of iron(II) chloride suspended in 13 ml of THF and one equivalent of a solution of deprotonated 5c gave, after removal of the solvent, the crude product 14e. The crude product was filtered through 5 cm of silica gel using a solvent mixture of $Et_2O/CH_2Cl_2$ in a ratio of 3:1. Taking off the solvent in an oil pump vacuum gave 176 mg (61%) of 14e as a blue powder. Gas-phase diffusion of $Et_2O$ into a concentrated $CH_2Cl_2$ solution of the complex enables deep blue single crystals to be obtained after 5 days.

1H-NMR: 0.69 (bs, 2H, $CH_2Cp$); 1.0–1.23 (m, 6H, $PCH_2CH_3$); 1.31 (s, 3H, $C_qCH_3$); 1.52 (bs, 4H, $PCH_2CH_3$); 1.83–2.71 (m, 4H, $CH_{2a,b}PPh_2$, $CH_{2a,b}PEt_2$); 3.71 (bs, 1H, Cp); 4.57 (bs, 1H, Cp); 4.93 (bs, 2H, Cp); 7.20–8.33 (m, 10H, aromat. H). 13C-NMR (193 K): 7.0, 8.7 (2s, $PCH_2CH_3$); 15.3 (d, $PCH_2CH_3$, $1J_{CP}$=12.8 Hz); 25.2 (d, $PCH_2CH_3$, $1J_{CP}$=20.2 Hz); 33.4 (m, $CH_2P$); 33.6 (t, $C_qCH_3$, $3J_{CP}$=9.2 HZ); 36.4 (s, $CH_2CP$); 44.5 (s, $C_q$); 58.0 ($C_{ipso}$), 85.6, 87.3 (3bs, Cp); 128.3–144.0 (m, aromat. C). 31P{1H}-NMR (193 K): 49.4 (d, $PPh_2$, $2J_{PP}$=95 Hz); 56.1 (d, $PEt_2$, $2J_{PP}$=95 Hz). CV ($CH_3CN$): $E_{1/2}$=–292 mV; DE=67 mV. MS (FAB): m/e (%) [frag.]: 498 (100%) [M+]; 463 (12%) [M+-Cl]. $C_{26}H_{33}P_2FeCl$ (498.798): calc. C 62.61, H 6.67, Cl 7.11, Fe 11.19, P 12.42; found. C 62.02, H 6.71.

Example 25
2,2-Bis(diphenylphosphinomethyl)-$\eta^5$-cyclopentadienylpropyl-iron(III) chloride hexafluorophosphate (14f)

Method A: Preparation from $FeCl_3$

In a 100 ml Schlenk tube, a solution of 0.13 g (0.77 mmol) of $FeCl_3$ in 10 ml of THF was injected at room temperature into one equivalent of a solution of deprotonated 5a over a period of 5 minutes. After about one third of the $FeCl_3$ solution had been added, the initially blue color of the reaction solution changed to a rust red. After stirring for 3 hours at room temperature, the solvent was removed in an oil pump vacuum. The residue was taken up in 10 ml of a solvent mixture of $CH_2Cl_2$/THF in a ratio of 3:1 and was filtered through 5 cm of silica gel in a G3 reversible frit. After removal of the solvent, the residue was taken up in 30 ml of EtOH and admixed with 0.13 g (0.77 mmol) of $NaPF_6$ to change the anion of the salt. After stirring for half an hour, the solvent was again removed and the residue was taken up in 10 ml of $CH_2Cl_2$. Filtration through 5 cm of silica gel and evaporation of the filtrate to dryness gave 360 mg (64%) of 14f as a rust red solid.

ESR: g=2.12 (298 K); $g_x$ 2.21, $g_y$ =2.11, $g_z$ 2.03 (100 K). MS (FAB); m/e (%) [frag.]: 594 (100%) [M+]; 559 (20%) [M+-Cl]; 504 (50%) [M+-Fe-Cl]. CV ($CH_3CN$): rev. red.: $E_{1/2}$=–171 mV; DE=72 mV. $C_{34}H_{33}F_6P_3FeCl$*1.5 $CH_2Cl_2$ (867.245); calc. C 49.13, H 4.15, Cl 16.38, Fe 6.46, F 13.15, P 10.73; found. C 48.99, H 4.38.

Method B: Preparation by oxidation of 14c

In a 100 ml Schlenk tube fitted with a septum, 0.24 g (0.4 mmol) of 14c was dissolved in 20 ml of $CH_2Cl_2$ and cooled to –70° C. At this temperature, a solution of 0.16 g (0.4 mmol) of $Ph_3CPF_6$ in 10 ml of $CH_2Cl_2$ was injected over a period of 2 minutes. During the addition, the color of the solution changed from blue via violet to a rust red.

The cooling bath was removed and the solution was stirred further for two hours. After removing the solvent, the residue was filtered through 5 cm of silica gel in a G3 reversible frit using a solvent mixture of $CH_2Cl_2$/THF in a ratio of 3:1. Removing the solvent again gave 0.21 g (70%) of 14f as a rust red powder. The ESR spectrum and the mass spectrum agree with those from preparation A).

Example 26
Reduction of 14f

Method A: Reduction with Na/Hg

In a 100 ml Schlenk tube, a solution of 0.16 g (0.98 mmol) of $FeCl_3$ in 10 ml of THF was injected at room temperature into one equivalent of a solution of deprotonated 5a over a period of 5 minutes. The solution was stirred for 2 hours at this temperature. The reaction solution was subsequently transferred into a 100 ml Schlenk tube in which 0.05 g of sodium had previously been dissolved in 2 ml of mercury. After about minutes, the suspension acquires a dark blue color and the solution is filtered through a G3 reversible frit. The solvent was removed completely and the residue was filtered through 10 cm of silica gel in a G3 reversible frit using a solvent mixture of $Et_2O/CH_2Cl_2$ in a ratio of 4:1. Taking off the solvent in an oil pump vacuum gave 0.29 g (48%) of a blue powder. The $^1$H-NMR spectrum and the mass spectrum agreed with those of 14c.

b) Reduction with phenyllithium:

In a 100 ml Schlenk tube a solution of 0.1 g (0.62 mmol) of $FeCl_3$ in 10 ml of THF was injected at room temperature into one equivalent of a solution of deprotonated 5a over a period of 5 minutes. The rust red solution was stirred for 2 hours at this temperature. 0.33 ml (0.66 mmol) of a 2 M solution of phenyllithium in cyclohexane/$Et_2O$ was subsequently injected into the above solution over a period of 1 minute. The cooling bath was removed and the reaction mixture was stirred further for 1 hour. During this time, the solution became dark blue. The solvent was removed completely and the residue was filtered through 10 cm of silica gel in a G3 reversible frit using a solvent mixture of $Et_2O/CH_2Cl_2$ in a ratio of 4:1. Removal of the solvent gave 0.31 g (52%) of a blue powder. The $^1$H-NMR spectrum and the mass spectrum agreed with those of 14c.

Example 27

2,2-Bis(diphenylphosphinomethyl)-$\eta^5$-cyclopentadienylpropyl-phenyl-iron(II) (14g)

In a 100 ml Schlenk tube fitted with a septum, 0.27 g (0.45 mmol) of 14c was dissolved in 20 ml of THF and cooled to −70° C. 0.23 ml (0.46 mmol) of a 2M solution of phenyllithium in cyclohexane/$Et_2O$ were injected into the blue solution in the Schlenk tube over a period of 1 minute. The cooling bath was subsequently removed and the mixture was stirred further for 2 hours. During this time, the solution became red-violet.

The solvent was removed in an oil pump vacuum and the residue was filtered through 5 cm of kieselguhr in a G3 reversible frit using a solvent mixture of $Et_2O/CH_2Cl_2$. The filtrate was evaporated in an oil pump vacuum, again giving a colorless precipitate. The residue was extracted with $Et_2O$ and the resulting red solution was freed completely of solvent in an oil pump vacuum. This gave 0.20 g (69%) of 14g as a red powder.

1H-NMR: 1.49 (bs, 3H, $CH_3$); 1.98 (bs, 2H, $CH_2Cp$); 2.20 (m, 2H, $CH_{2a}P$, $2J_{HH}$=14.2 Hz, $2J_{HP}$=4.6 Hz, $4J_{HP}$=4.4 Hz); 2.40 (m, 2H, $CH_{2b}P$, $2J_{HH}$=13.2 Hz, $2J_{HP}$=4.6 Hz, $4J_{HP}$=4.4 Hz); 3.99 (bs, 2H, Cp); 4.25 (bs, 2H, Cp); 6.45–8.05 (m, 25H, aromat. H). 13C{1H}-NMR: 33.7 (t, $CH_3$); 38.6 (s, $CH_2Cp$); 40.0 (pt, $CH_2P$, $1J_{CP}$=8.5 Hz, $3J_{CP}$=7.8 Hz); 45.2 (t, $C_q$, $2J_{CP}$=2.2 Hz); 75.7 ($C_{ipso}$), 80.7, 88.9 (3s, Cp); 119.8 (s, $C_{para}$ of Ph—Fe); 124.1–145.3 (m, aromat. C); 150.1 (s, $C_{ipso}$ of Ph—Fe). 31P{1H}-NMR: 60.4 (s). MS (FAB); m/e (%) [frag.]: 636 (25%) [M+]; 581 (100%) [M+-Fe]; 503 (55%) [M+-Fe—$C_6H_5$]. $C_{40}H_{38}FeP_2$ (636.536): calc. C 75.45, H 6.02, Fe 8.79, P 9.74; found. C 74.32, H 6.46.

Example 28

2,2-Bis(diphenylphosphinomethyl)-$\eta^5$-cyclopentadienylpropyl(acetonitrile)iron(II) hexafluorophosphate (14h)

In a 100 ml Schlenk tube, 0.30 g (0.5 mmol) of 14c was dissolved in 20 ml of $CH_3CN$. 0.09 g (0.53 mmol) of $NaPF_6$ was added to this dark blue solution and the mixture was stirred for 8 hours at room temperature. During this time, the color of the reaction solution changed from blue to bright red. The solvent was removed in an oil pump vacuum, the residue was taken up in 10 ml of $CH_2Cl_2$ and filtered through 5 cm of silica gel. The red filtrate was evaporated to dryness in an oil pump vacuum, giving 0.28 g (75%) of 14 h as a red powder.

1H-NMR: 1.52 (bs, 2H, $CH_2Cp$); 1.58 (t, 3H, $CH_3C_q$, $4J_{HP}$=3.1 Hz); 2.32 (m, 2H, $CH_{2a}P$, $2J_{HH}$=15.6 Hz, $2J_{HP}$=4.6 Hz, $4J_{HP}$=4.5 Hz); 2.54 (s, 3H, $CH_3CN$); 2.64 (m, 2H, $CH_{2b}P$, $2J_{HH}$=15.6 Hz, $2J_{HP}$=4.6 Hz, $4J_{HP}$=4.5 Hz); 4.16 (m, 2H, Cp); 5.08 (m, 2H, Cp); 6.74–7.92 (m, 20H, aromat. H). 31P{1H}-NMR: 52.5 (s, $CH_2P$); −144.3 (sept, $PF_6$). 13C{1H}-NMR: 6.7 (s, $CH_3CN$); 33.2–33.8 (m, $CH_3$, $CH_2P$); 36.3 (s, $CH_2Cp$); 46.0 (s, $C_q$); 68.8 ($C_{ipso}$), 80.7, 92.3 (3s, Cp); 128.5–143.3 (m, $CH_3CN$, aromat. C). MS (FAB); m/e (%) [frag.]: 600 (20%) [M+], 559 (100%) [M+-$CH_3CN$]; 503 (70%) [M+-Ph]. IR (CsI): 2255 cm-1 (w). CV ($CH_3CN$): rev. ox.: $E_{1/2}$=535 mV; DE=70 mV. $C_{36}H_{36}F_6FeNP_3$ (745.446): calc. C 57.99, H 4.83, F 15.30, Fe 7.52, N 1.88, P 12.48; found. C 58.38, H 5.14, N 1.39, P 12.26.

Example 29

General method of preparing lithium diarylphosphides and lithium dibenzophospholide One equivalent of N-BuLi solution in hexane (about 2.3 M) was added dropwise at 0° C. to an approximately 0.3 M solution of the diarylphosphine or 5-H-dibenzophosphole in THF over a period of about 5 minutes. The solution was subsequently stirred further for at least half an hour. The red solutions prepared in this way were used directly for syntheses.

Example 30

3-(Cyclopentadienylmethyl)-3-(diphenylphosphino-methyl) oxetane (2a)

In a 250 ml Schlenk tube fitted with a septum 2.6 g (10 mmol) of 1a were dissolved in 50 ml of THF and the solution was cooled to −5° C. At this temperature, one equivalent of a diphenylphosphide solution was added dropwise via a capillary hose to the oxetane solution over a period of 2 hours. After the addition was complete, the mixture was stirred further for half an hour at room temperature.

During this time, 5.2 g (17 mmol) of $CpMgCl*2THF$ were dissolved in 50 ml of THF in a 250 ml three-neck flask fitted with reflux condenser, septum and inert gas connection and the solution was heated to 60° C. The solution of the oxetane was then added dropwise via a capillary hose over a period of 45 minutes. After the addition was complete, the reaction solution was boiled for a further three hours.

The work-up was carried out by addition of 100 ml of 10% strength ammonium chloride solution. After separating off the organic phase, the aqueous phase was extracted twice with 30 ml each time of diethyl ether and the combined organic phases were subsequently washed with sodium chloride solution until neutral. After removing the solvent, the resulting viscous, colorless residue was dissolved in methylene chloride and absorbed on kieselguhr. Flash chromatography on a silica gel column (25*4 cm; eluant: PE/THF in a ratio of 9:1; $R_F$=0.38) gives, after evaporating the product fraction in an oil pump vacuum, 2 g (60 %) of 2a in the form of a colorless oil.

MS (EI); m/e (%) [frag.]: 334 (98%)[M$^+$]; 303 (75%) [M$^+$-$CH_2O$—H]; 183 (100%) [$PPh_2^+$-2H]. $C_{22}H_{22}OP$ (333.390): calc. C 79.04, H 6.89, O 4.79, P 9.28; found. C 74.27, H 6.88.

Example 31

2,2-Bis(diphenylphosphinomethyl)-3-cyclopenta-dienyl-1-propanol (3a)

In a 250 ml three-neck flask fitted with reflux condenser, septum and inert gas connection, 2 g (6 mmol) of 2a were dissolved in 50 ml of THF and were deprotonated at 0° C. by injecting in 2.5 ml (6 mmol) of n-BuLi solution. The mixture was stirred further for half an hour. Via a capillary hose, 1.2 equivalents of a diphenylphosphide solution were added dropwise at room temperature over a period of half an hour. The reaction solution was subsequently refluxed for 3 hours, during which time the red color slowly changed to orange.

The reaction mixture was evaporated in an oil pump vacuum and the residue was taken up in 50 ml of diethyl ether. Hydrolysis was carried out by adding 20 ml of water and stirring for 10 minutes. The organic phase was separated off and the aqueous phase was extracted twice with 30 ml of diethyl ether. The combined ether phases were washed with sodium chloride solution until neutral and dried over sodium sulfate. The colorless oil which remained was dissolved in methylene chloride and absorbed on kieselguhr. This was followed by flash chromatography on silica gel (25*4 cm; eluant: PE/diethyl ether in a ratio of 8.5:1.5; $R_F$=0.26). This gave 1.3 g (42%) of 3a as a colorless, viscous oil.

MS (EI); m/e (%) [frag.]: 520 (60%) [M+]; 443 (100%) [$M^+$-$C_6H_5$]; 335 (75%) [$M^+$-$PPh_2$]; 185 (30%) [$PPh_2^+$]; 183 (65%) [$PPh_2^+$-2H]. $C_{34}H_{34}OP_2$ (520.591): calc. C 78.46, H 6.54, O 3.08, P 11.92; found. C 76.17, H 6.73.

Example 32
3-Cyclopentadienyl-2-(di-m-xylylphosphinomethyl)-2-(diphenylphosphinomethyl)-1-propanol (3b)

The preparation was carried out using a method similar to that for 3a. 1.4 g (4.2 mmol) of 2 were deprotonated with 1.8 ml (4.2 mmol) of n-BuLi solution and 1.2 equivalents of lithium di-m-xylylphosphide solution to give the crude product 3b. The colorless oil which remained was dissolved in methylene chloride and absorbed on kieselguhr. This was followed by flash chromatography on silica gel (20*4 cm; eluant: PE/diethyl ether in a ratio of 8.75:1.25; $R_F$=0.31). This gave 1.15 g (47%) of 3b as a colorless, viscous oil.

MS (EI); m/e (%) [frag.]: 576 (83%) [$M^+$]; 499 (100% [$M^+$-$C_6H_5$]; 471 (75%) [$M^+$-$C_6H_5$—$CH_2O$]; 391 (90%) [$M^+$-$PPh_2$]; 241 (65%) [$P(m-XYl)_2^+$]; 185 (20%) [$PPh_2^+$]. $C_{38}H_{42}OP_2$ (576.689): calc. C 79.17, H 7.29, O 2.78, P 10.76; found. C 78.34, H 7.55.

Example 33
3-Cyclopentadienyl-2-(5-dibenzophospholylmethyl)-2-(diphenylphosphinomethyl)-1-propanol (3c)

The preparation was carried out using a method similar to that for 3a. 1.6 g (4.8 mmol) of 2a were deprotonated with 2 ml (4.8 mmol) of n-BuLi solution and reacted with 1.2 equivalents of lithium dibenzophospholide solution to give the crude product 3c. The colorless oil which remained was dissolved in methylene chloride and absorbed on kieselguhr. This was followed by flash chromatography on silica gel (23*4 cm; eluant: PE/diethyl ether in a ratio of 8.5:1.5, $R_F$=0.27). This gave 1.36 g (55%) of 3c in the form of a colorless, viscous oil.

MS (EI); m/e (%) [frag.]: 518 (40%) [M+];439 (20%) [$M^+$-$C_6H_5$]; 335 (60%) [$M^+$-DBP]; 183 (100%) [$DBP^+$]. $C_{34}H_{32}OP_2$ (518.575): calc. C 78.75, H 6.22, O 3.09, P 11.95; found. C 77.08, H 6.56.

Example 34
2,2-Bis(diphenylphosphinomethyl)-3-cyclopentadienyl-1-propyl acetate (4a)

In a 250 ml three-neck flask fitted with reflux condenser, septum and inert gas connection, 4.26 g (12.5 mmol) of 2a were dissolved in 50 ml of THF and deprotonated by injection of 5.2 ml (12.5 mmol) of n-BuLi solution at 0C. The mixture was stirred further for half an hour. via a capillary hose, 1.2 equivalents of a diphenylphosphide solution were added dropwise at room temperature over a period of half an hour. After removing the solvent, the crude product was taken up in 50 ml of toluene and, at room temperature, 1.6 ml (22.8 mmol) of acetyl chloride were slowly injected into this orange-red solution. A colorless precipitate indicated the formation of the ester. During this procedure, the solution warmed up and became red.

The solution was hydrolyzed by addition of 100 ml of degassed water containing 1 ml of pyridine. The mixture was stirred further for 10 minutes and, after phase separation, the organic phase was separated off. After extracting the aqueous phase twice with 50 ml of toluene, the combined toluene phases were washed with sodium chloride solution until neutral and dried over sodium sulfate. The solution was substantially freed of solvent and the resulting viscous oil was taken up in methylene chloride. Absorption on kieselguhr and flash chromatography on silica gel (25*4 cm; eluant: PE/diethyl ether in a ratio of 8.5:1.5; $R_F$=0.26) give 2.4 g (34%) of 4a in the form of a colorless oil.

MS (EI); m/e (%) [frag.]: 562 (63%) [$M^+$]; 485 (100%) [$M^+$-$C_6H_5$]; 377 (95%) [$M^+$-$PPh_2$]; 183 (65%) ($PPh_2^+$-2H]. $C_{36}H_{36}O_2P_2$ (562.628): calc. C 76.87, H 6.41, O 5.69, P 11.03; found. C 75.93, H 6.56.

Example 35
3-Benzylthiomethyl-3-cyclopentadienyloxetane (1b)

The benzylthiolate solution was first prepared in a baked-out 250 ml Schlenk tube fitted with a septum. For this purpose, 2.00 g (16.1 mmol) of benzyl thiol were dissolved in 50 ml of THF and were deprotonated at 0° C. by injecting in 6.7 ml (16.1 mmol) of n-BuLi solution. The solution was then stirred at room temperature for at least half an hour. During this time, 4.37 g (16.89 mmol) of la were dissolved in 50 ml of THF in a further 250 ml Schlenk tube fitted with a septum and the solution was cooled to −15° C. The benzylthiolate solution was slowly added dropwise to the oxetane solution over a period of 2 hours. After the addition was complete, the mixture was stirred further for half an hour at room temperature. During this time, 5.9 g (22 mmol) of CpMgCl*2THF were dissolved in 50 ml of THF in a 250 ml three-neck flask fitted with reflux condenser, septum and inert gas connection and the solution was heated to 60° C. The solution of the oxetane was added dropwise to the Grignard solution over a period of 45 minutes. After the addition was complete, the reaction mixture was boiled for another 3 hours. It was worked up by addition of 100 ml of 10% strength ammonium chloride solution. After separating off the organic phase, the aqueous phase was extracted three times with 30 ml each time of diethyl ether and the combined organic phases were subsequently washed with sodium chloride solution until neutral. The solvent was taken off in an oil pump vacuum, the resulting viscous, colorless residue was dissolved in methylene chloride and absorbed on kieselguhr. Flash chromatography on a silica gel column (25*4 cm; eluant: PE/THF in a ratio of 8.7:1.3; $R_F$=0.39) and evaporation of the product fraction in an oil pump vacuum give 3.08 g (67%) of lb as a colorless oil.

MS (EI); m/e (%) [frag.]: 272 (25%) [$M^+$], 181 (100%) [$M^+$-$CH_2Ph$], 91 (50%) [$CH_2Ph^+$]. $C_{17}H_{20}OS$ (272.413).

Example 36
2-Benzylthiomethyl-3-cyclopentadienyl-2-diphenylphosphinomethyl-1-propanol (3d)

In a 250 ml three-neck flask fitted with reflux condenser, septum and inert gas connection, 2.77 g (10.2 mmol) of lb were dissolved in 50 ml of THF and deprotonated at 0° C. by injection of 4.4 ml (10.2 mmol) of n-BuLi solution. The mixture was stirred further for half an hour. Via a capillary hose, 1.2 equivalents of a diphenylphosphide solution were added dropwise at room temperature over a period of half an hour. The reaction solution was stirred for 16 hours at this temperature and the solvent was subsequently substantially removed. The residue was taken up in 50 ml of diethyl ether and hydrolyzed with 20 ml of water. The organic phase was separated off and the aqueous phase was extracted twice with 30 ml of diethyl ether. The combined ether phases were washed with sodium chloride solution until neutral and dried over sodium sulfate. The colorless oil which remained was dissolved in methylene chloride and absorbed on kieselguhr. This was followed by flash chromatography on silica gel (25*4 cm; eluant: PE/diethyl ether in a ratio of 8.75:1.25; $R_F$=0.29). This gives 1.9 g (40 %) of 3d in the form of a colorless, viscous oil.

MS (EI);m/e (%) [frag.]: 458 (3%) [M$^+$]; 367 (100%) [M$^+$-CH$_2$PPh$_2$]; 217 (25%) [SPPh$_2^+$]; 183 (30%) [PPh$_2^+$-2H]. C$_{29}$H$_{31}$OPS (457.598): calc. C 75.98, H 6.77, O 3.49, S 6.99, P 6.77; found. C 74.38, H 7.10.

Example 37

Method of preparing the deprotonated ligands 3a and 4a:

One equivalent of n-BuLi solution in hexane (about 2.3 M) was injected at 0° C. into an approximately 0.05 M solution of the ligands 3a and 4a in THF and the resulting slightly yellowish solutions were stirred further for at least half an hour.

Example 38

2,2-Bis(diphenylphosphinomethyl)-3-$\eta^5$-cyclopentadienyl-1-propanol-iron(II) chloride (14a)

In a 100 ml Schlenk tube, 0.32 g (0.49 mmol) of bis(triphenylphosphine)iron(II) chloride was dissolved in 30 ml of THF and cooled to −70° C. One equivalent of a solution of deprotonated 3a was added thereto over a period of 2 minutes. After an initial red coloration, the solution acquired a dirty blue color. The mixture was stirred for 15 minutes at this temperature and the cooling bath was then removed. Stirring was then continued for a further 2 hours. During this time, a brownish precipitate formed. The solvent was removed and the residue was transferred onto 5 cm of silica gel in a G3 reversible frit. A slightly greenish fraction was separated off by washing with 30 ml of a 2:1 mixture of PE and diethyl ether. The product was eluted as a dark blue fraction using a 4:1 mixture of diethyl ether and methylene chloride. Removal of the solvent in an oil pump vacuum gave 0.19 g (64%) of 14a in the form of a dark blue powder.

1H-NMR (CH$_2$Cl$_2$): 1.19 (2H, CH$_2$Cp); 2.26 (m, 2H, CH$_{2a}$P, 2J$_{HH}$= 16.1 Hz); 2.77 (m, 2H, CH$_{2b}$P); 3.73 (bs, 2H, CH$_2$OH); 3.96 (bs, 2H, Cp); 4.95 (bs, 2H, Cp); 6.62–8.26 (m, 20H, aromat. H). 31P{1H}-NMR (CH$_2$Cl$_2$, 223K): 44.6 (bs). MS (FAB); m/e (%) [frag.]: 610 (100%) [M+]; 575 (25%) [M+-Cl]. C$_{34}$H$_{33}$P$_2$FeCl (610.890): calc. C 66.87, H 5.45, P 10.15, O 2.62, Cl 5.73, Fe 9.18; C 65.33, H 5.56, P 9.44.

Example 39

(2,2-Bis(diphenylphosphinomethyl)-3-$\eta^5$-cyclopentadienyl-1-propyl acetate)iron(II) chloride (14b)

In a 100 ml Schlenk tube, 0.4 g (0.62 mmol) of bis(triphenylphosphine)iron(II) chloride was dissolved in 30 ml of THF and cooled to −70° C. One equivalent of a solution of deprotonated 4a was added thereto over a period of 2 minutes. After an initial red coloration, the solution acquired a blue-green color. The mixture was stirred for 15 minutes at this temperature and the cooling bath was then removed. Stirring was then continued for a further two hours. During this time, a brownish precipitate formed. The solvent was taken off in an oil pump vacuum and the residue was transferred to 5 cm of silica gel in a G3 reversible frit. A slightly greenish fraction was separated off by washing with 30 ml of a 2:1 mixture of PE and diethyl ether. The product was eluted as a deep blue fraction using a 4:1 mixture of diethyl ether and methylene chloride. Removal of the solvent in an oil pump vacuum gave 0.18 g (44%) of 14b in the form of a dark blue powder.

1H-NMR (CH$_2$Cl$_2$): 1.31 (2H, CH$_2$Cp); 2.21 (3H, CH$_3$CO$_2$); 2.26–2.34 (m, 2H, CH$_{2a}$P); 2.63–2.73 (m, 2H, CH$_{2b}$P); 3.76 (bs, 2H, CH$_2$O); 3.97 (bs, 2H, Cp); 4.98 (bs, 2H, Cp); 6.62–8.27 (m, 20H, aromat. H). 31P{1H}-NMR (CH$_2$Cl$_2$, 295K): 44.6 (bs). MS (FAB); m/e (%) [frag.]: 652 (100%) [M+]; 617 (70%) [M+-Cl]. C$_{36}$H$_{35}$ClFeO$_2$P$_2$ (652.927): calc. C 66.16, H 5.38, Cl 5.48, Fe 8.58, O 4.90, P 9.50; found. C 66.20, H 5.80, P 9.36.

Example 40

$\eta^2$-2,2-Bis(diphenylphosphinomethyl)-$\eta^5$-cyclopenta-dienylpropyl-(dicarbonyl)molybdenum(II) iodide (15a)

In a 100 ml Schlenk tube fitted with a septum, 0.30 g (0.59 mmol) of 5a was dissolved in 20 ml of THF and deprotonated at 0° C. with 0.26 ml (0.59 mmol) of 2.3 M n-BuLi solution. After removing the cooling, the mixture was stirred further for 30 minutes. 1.3 ml (1.3 mmol) of borane-THF complex were subsequently injected in at room temperature. The solution was stirred further for 15 minutes and was evaporated to dryness in an oil pump vacuum.

The residue was again taken up in 30 ml of THF and, at room temperature, 0.18 g (0.59 mmol) of Mo(CH$_3$CN)$_3$(CO)$_3$ was added. The initial suspension turned into a brown solution over a period of 5 minutes. This was stirred for 2 hours at room temperature and, while cooling in ie. a solution of 0.15 g (1.3 mmol) of iodine in 10 ml of THF was added dropwise by means of a syringe. The red-brown reaction mixture was stirred for 3 hours and the solvent was removed in an oil pump vacuum. The residue was taken up in 5 ml of toluene and filtered through 5 cm of silica gel in a G3 reversible frit. The product ran through the silica gel as a sharp red band. In the IR spectrum, the product displayed two carbonyl bands at ν=2038 and 1962 cm−$^1$.

The red toluene solution obtained was evaporated to half its volume in an oil pump vacuum and 0.15 g (1.3 mmol) of DABCO was added. The solution was heated to 70° C. on a water bath and stirred for 2 hours at this temperature. A yellow precipitate formed during this time. The reaction mixture was evaporated to 5 ml and chromatographed on silica gel (10*2 cm) using toluene as eluant. The product ran through as a strongly colored red band. The solvent was taken off completely in an oil pump vacuum, giving 0.38 g (76%) of 15a in the form of a red powder.

1H-NMR (CDCl$_3$): 0.81 (bs, 3H, CH$_3$); 2.10 (bs, 2H, CH$_2$Cp); 2.30–2.57 (m, 4H, CH$_2$P, CH$_2$PMo); 4.93, 4.99, 5.67, 5.68 (4s, 4H, Cp); 7.27–7.59 (m, 20H, aromat. H). 13C{1H}-NMR (CDCl$_3$): 29.7 (m, CH$_3$); 36.8–38.5 (m, CH$_2$P, CH$_2$PMo, C$_q$); 46.0, 46.3 (2d, CH$_2$Cp, 3J$_{CP}$=14 Hz); 76.5 (C$_{ipso}$), 77.0 (C$_{ipso}$), 87.7, 88.2, 95.4, 96.0, 100.1, 100.2 (8s, Cp$_a$, Cp$_b$); 128.13–140.9 (m, aromat. C). 31P{1H}-NMR (CDCl$_3$): 47.6 (s, MoPPh$_2$); −26.3 (s, PPh$_2$). IR (toluene): 1964 (s); 1959 (sh); 1887 (vs); 1859 (sh) cm−1. MS (FAB); m/e (%) [frag.]: 783 (8%) [M+]; 728 (100%) [M+-2CO]; 651 (30%) [M+-I]. C$_{36}$H$_{33}$IMoO$_2$P$_2$ (782.442): calc. C 55.24, H 4.22, I 16.24, Mo 12.28, O 4.09, P 7.93; found. C 54.47, H 4.95, P 7.65.

Example 41

2,2-Bis(diphenylphosphinomethyl)-$\eta^5$-cyclopentadienylpropyl-(dicarbonyl)molybdenum(II) iodide (15b)

0.7 g (0.9 mmol) of 15a was weighed into a 100 ml Carius tube with a Teflon closure and taken up in 40 ml of toluene. The Carius tube was closed and irradiated for 48 hours using an external, coolable radiation source (high-pressure mercury vapor lamp). During this time, an ocher-colored precipitate was formed. At the end of the irradiation, the solution was slightly yellowish. The precipitate was separated off in a G3 reversible frit, washed three times with 10 ml of THF and once with 10 ml of diethyl ether and was dried in an oil pump vacuum. This gave 0.51 g (72%) of 15b in the form of a yellow-ocher powder. Yellow single crystals suitable for X-ray structural analysis were obtained by gas-phase diffusion of diethyl ether into a solution of 15b in methylene chloride for 7 days.

1H-NMR (CD$_2$Cl$_2$): 1.82 (bs, 3H, CH$_3$); 2.43 (d, 2H, CH$_{2a}$P, 2J$_{HH}$=15.1 Hz); 2.67–2.73 (m, 4H, CH$_{2b}$P, CH$_2$Cp); 4.95, 5.60 (2bs, 2H, Cp); 6.95–7.42 (m, 20H, aromat. H). 13C{1H}-NMR (CD$_2$Cl$_2$): 34.5–35.0 (m, CH$_3$, CH$_2$P); 36.1 (s, CH$_2$Cp); 44.1 (t, C$_q$, 2J$_{CP}$=3.7 Hz); 91.3, 98.2 (2s, Cp); 102.5 (1s, Cp, C$_{ipso}$); 129.0–141.6 (m, aromat. C); 238.5 (m, CO). 31P{1H}-NMR (CD$_2$Cl$_2$): 45.2 (s). IR (THF): 1969 (vs), 1901 (s) cm$^{-1}$. MS cation (FAB); m/e (%) [frag.]: 657 (100%) [M+]; 629 (15%) [M+-CO]; 601 (20%) [M+-2CO]. MS anion (FAB): 127 [I–]. C$_{36}$H$_{33}$IMoO$_2$P$_2$ (782.442): calc. C 55.24, H 4.22, I 16.24, Mo 12.28, O 4.09, P 7.93; found. C 54.18, H 4.56.

Example 42

2,2-Bis(diphenylphosphinomethyl)-η$^5$-cyclopentadienylpropyl-oxo-molybdenum(IV) iodide, (15c)

0.78 g (1 mmol) of 15a was dissolved in 100 ml of toluene in an irradiation apparatus. The remaining gas space of the apparatus was mixed with air and the red solution was irradiated for 48 hours at 20° C. with vigorous stirring. During this time, a red-violet precipitate was formed. The precipitate was separated off in a G3 reversible frit and washed with THF until the filtrate remained colorless. The precipitate which remained was subsequently eluted with a 4:1 mixture of methylene chloride and THF and the bright red eluate was freed of solvent in an oil pump vacuum. This gave 0.48 g (65%) of 15c as a red-violet powder. Red-violet single crystals could be obtained by gas-phase diffusion of diethyl ether into an ethanol/methylene chloride solution (4:1) of the complex at 30C after 7 days.

1H-NMR (CD$_2$Cl$_2$): 1.75 (t, 3H, CH$_3$, 3J$_{HP}$=3.2 Hz); 2.01 (bs, 2H, CH$_2$Cp); 2.50, 2.79 (2ddd, 2H, CH$_{2a,b}$P, 2J$_{HH}$=16.3 Hz, 2J$_{HP}$=4.5 Hz, 4J$_{HP}$=4 Hz); 5.25 (sh, 2H, Cp); 5.98 (bs, 2H, Cp); 7.00–7.76 (m, 20H, aromat. H). 13C{1H}-NMR (CD$_2$Cl$_2$): 31.9 (t, CH$_2$P, 1J$_{CP}$=15.2 Hz); 34.6 (bs, CH$_3$); 36.1 (s, CH$_2$Cp); 44.1 (s, C$_q$); 95.2, 107.8 (2s, Cp), 110.5 (s, Cp, C$_{ipso}$); 128.8–138.5 (m, aromat. C). 31P{1H}-NMR (CD$_2$Cl$_2$): 51.6 (s). IR (C$_{ipso}$): n$_o$=919 (s). MS (FAB); m/e (%) [frag.]: 617 (100%) [M+-I]; 503 (25%) [M+-I-Mo-O]. C$_{34}$H$_{33}$IMoOP$_2$*CH$_2$Cl$_2$ (827.367): calc. C 50.81, H 4.26, C 18.57, I 15.34, Mo 11.60, O 1.93, P 7.49; found. C 50.36, H 4.39.

Formulae

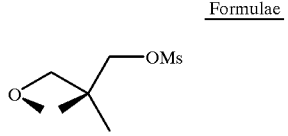

1

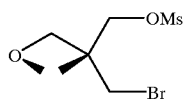

1a

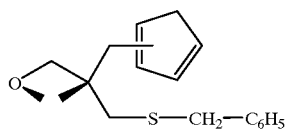

1b

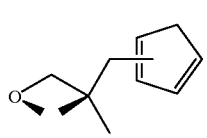

2

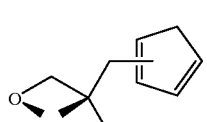

2a

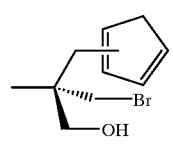

3

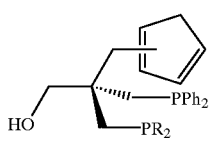

3a PR$_2$ = PPh$_2$
3b PR$_2$ = P(m-xylyl)$_2$

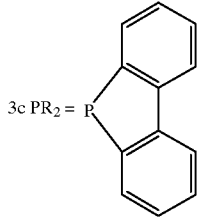

3c PR$_2$ =

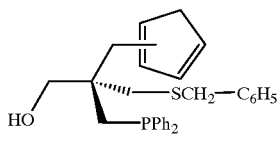

3d

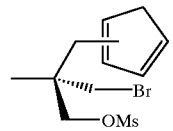

4

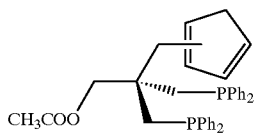

4a

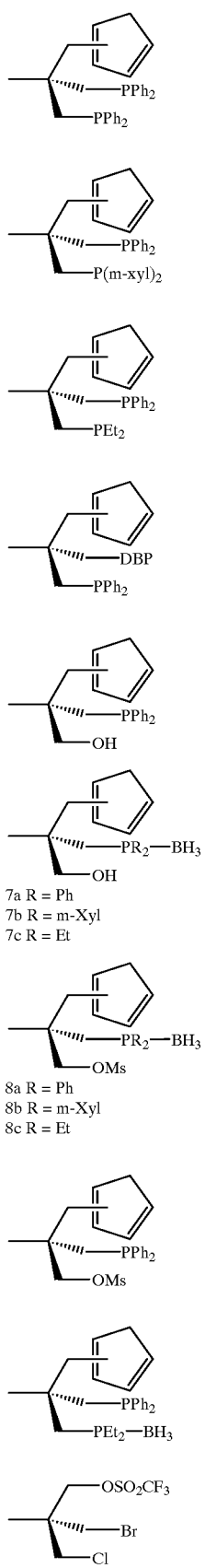
7a R = Ph
7b R = m-Xyl
7c R = Et
8a R = Ph
8b R = m-Xyl
8c R = Et
14a R = H
14b R = CH₃—C(=O)—
14c R = Ph
14d R = m-xylyl
14e R = Et -continued

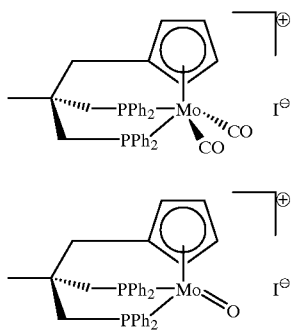

15b

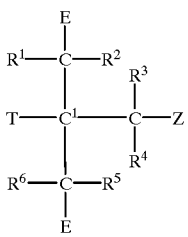

15c

We claim:

1. A tripodal cyclopentadiene derivative of the formula (I)

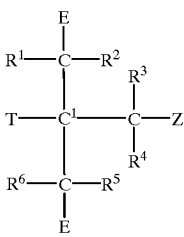

(I)

where

C$^1$ is a spiro carbon atom,

E are identical or different and are —N(R)(R), —P(R)(R), —As(R)(R), —Sb(R)(R), —OR, —SR, —SeR, —TeR, where R are identical or different and are each hydrogen, a C$_1$–C$_{20}$-carboorganic radical or a C$_1$–C$_{30}$-organosilicon radical, or E is a leaving group X and R$^1$, R$^2$, R$^3$, R$^4$, R$^5$, R$^6$ are identical or different and are each hydrogen, a C$_1$–C$_{20}$-carboorganic radical or a C$_1$–C$_{30}$-organosilicon radical, Z is a C$_5$–C$_{50}$-cyclopentadienyl structural unit and T is hydrogen, a C$_1$–C$_{20}$-carboorganic radical or a C$_1$–C$_{30}$-organosilicon radical or a group E—Y—, where E is —N(R)(R), —P(R)(R), —As(R)(R), —Sb(R)(R), —OR, —SR, —SeR, —TeR or a leaving group X, where R are identical or different and are each hydrogen, a C$_1$–C$_{20}$-carboorganic radical or a C$_1$–C$_{30}$-organosilicon radical and Y is a C$_1$–C$_{20}$-organic group which connects E to C$^1$.

2. A tripodal cyclopentadiene derivative as claimed in claim 1, wherein E are identical or different and are each —P(R)(R).

3. A tripodal cyclopentadiene derivative as claimed in claim 1, wherein Z is a cyclopentadienyl radical or a cyclopentadienyl radical substituted by from one to four C$_1$–C$_{10}$-alkyl groups.

4. A tripodal cyclopentadiene derivative as claim 1, wherein T is a C$_1$–C$_{10}$-alkyl radical and E—Y— is —CH$_2$—OR.

5. A tripodal cyclopentadiene derivative claim 1, wherein T is —CH$_2$—OR and R is hydrogen or a C$_1$–C$_{10}$-carboorganic radical.

6. A process for preparing tripodal cyclopentadiene derivatives of the formula (I)

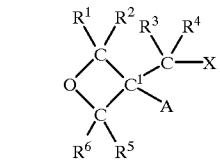

(I)

by reacting an oxetane derivative of the formula (II)

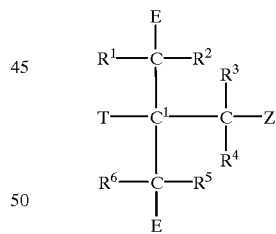

(II)

where

R$^1$,R$^2$,R$^3$,R$^4$,R$^5$,R$^6$ are identical or different and are each hydrogen, a C$_1$–C$_{20}$-carboorganic radical or a C$_1$–C$_{30}$-organosilicon radical, A is hydrogen, a C$_1$–C$_{20}$-carboorganic radical or a C$_1$–C$_{30}$-organosilicon radical and X is a leaving group, with (a) one C$_{5-C50}$-cyclopentadienyl anion equivalent with replacement of X to form the cyclopentadienyl-substituted oxetane derivative, (b) ring opening of the cyclopentadienyl-substituted oxetane derivative by means of an acid H—X, (c) conversion of the —OH function formed into a leaving group X and (d) replacement of the leaving group X by E.

7. A process for preparing tripodal cyclopentadiene derivatives of the formula (I)

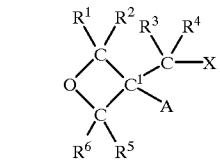

(I)

by reacting an oxetane derivative of the formula (II)

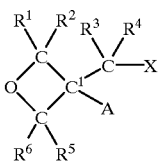

(II)

where

R$^1$,R$^2$,R$^3$,R$^4$,R$^5$,R$^6$ are identical or different and are each hydrogen, a C$_1$–C$_{20}$-carboorganic or a C$_1$–C$_{30}$-organosilicon radical, A is hydrogen, a $C_1$–$C_{20}$-carboorganic radical or a $C_1$–$C_{30}$-organosilicon radical and X is a leaving group, with (a) one $C_{5-C50}$-cyclopentadienyl anion equivalent with replacement of X to form the cyclopentadienyl-substituted oxetane derivative, (b) nucleophilic ring opening of the cyclopentadienyl-substituted oxetane derivative by means of $MetE_n$, where Met is an element of the first, second or third main group of the Periodic Table of the Elements, n is the maximum formal valence of Met in the compound $MetE_n$ and E is as defined for formula (I), with the leaving group X being excluded, (c) conversion of the OH function formed into a leaving group X, (d) replacement of the leaving group X by E.

8. A process for preparing chiral, tripodal cyclopentadiene derivatives as claimed in claim 7, wherein different substituents E are introduced in (b) and (d).

9. A process for preparing functionalized, tripodal cyclopentadiene derivatives of the formula (III)

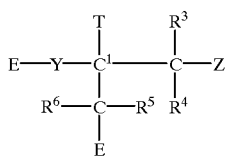

(III)

where

E are identical or different and are —N(R)(R), —P(R)(R), —As(R)(R), —Sb(R)(R), —OR, —SR, —SeR, —TeR, where R are identical or different and are each hydrogen, a $C_1$–$C_{20}$-carboorganic radical or a $C_1$–$C_{30}$-organosilicon radical, or E is a leaving group X and Y is a $C_1$–$C_{20}$-organic group which connects E to $C^1$, $R^3$, $R^4$, $R^5$, $R^6$ are identical or different and are each hydrogen, a $C_1$–$C_{20}$-carboorganic radical or a $C_1$–$C_{30}$-organosilicon radical, Z is a $C_5$–$C_{50}$-cyclopentadienyl structural unit and T is RO—C($R^1$)($R^2$)—, where R, $R^1$ and $R^2$ are identical or different and are each hydrogen or a $C_1$–$C_{10}$-carboorganic radical, by reacting an oxetane derivative of the formula (II)

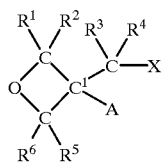

(II)

where $R^1$, $R^2$, $R^3$, $R^4$, $R^5$, $R^6$ are identical or different and are each hydrogen, a $C_1$–$C_{20}$-carboorganic radical or a $C_1$–$C_{30}$-organosilicon radical, A is a structural unit —Y—X, where X is a leaving group and Y is a $C_1$–$C_{20}$-organic group which connects X to $C^1$, X is a leaving group with (a) $MetE_n$ where Met is an element of the first, second or third main group of the Periodic Table of the Elements, n is the maximum formal valence of Met in the compound $MetE_n$ and E is as defined for formula (I), with the leaving group X being excluded, (b) one cyclopentadienide anion equivalent or one $C_{5-C50}$-cyclopentadienyl anion equivalent, (c) nucleophilic ring opening of the cyclopentadienyl-substituted oxetane derivative by means of $MetE_n$, where Met is an element of the first, second or third main group of the Periodic Table of the Elements, n is the maximum formal valence of Met in the compound $MetE_n$ and E is as defined for formula (I), with the leaving group X being excluded, (d) optionally modifying the OH function formed to give the group t, (e) optionally replacing RO— in the group T by a leaving group X.

10. A process for preparing chiral, functionalized tripodal cyclopentadiene derivatives as claimed in claim 9, wherein the substituents E are different in (a) and (c).

11. A tripod metal complex of the formula (V)

$$L_nM(T_p)_m \qquad (V)$$

where

M is a transition metal or a main group metal of the Periodic Table of the Elements, $T_p$ is a cyclopentadiene derivative of the formula (I)

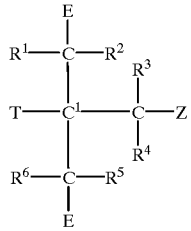

(I)

or its conjugate anion,

E are identical or different and are —N(R)(R), —P(R)(R), —As(R)(R), —Sb(R)(R), —OR, —SR, —SeR, —TeR, where R are identical or different and are each hydrogen, Ad $C_1$–$C_{20}$-carboorganic radical or a $C_1$–$C_{30}$-organosilicon radical, or E is a leaving group X and $R^1$, $R^2$, $R^3$, $R^4$, $R^5$, $R^6$ are identical or different and are each hydrogen, a $C_1$–$C_{20}$-carboorganic radical or a $C_1$–$C_{30}$-organosilicon radical, Z is a $C_{5-C50}$-cyclopentadienyl structural unit and T is hydrogen, a $C_1$–$C_{20}$-carboorganic radical or a $C_1$–$C_{30}$-organosilicon radical or a group E—Y—, where E is —N(R)(R), —P(R)(R), —As(R)(R), —Sb(R)(R), —OR, —SR, —SeR, —TeR or a leaving group X, where R are identical or different and are each hydrogen, a $C_1$–$C_{20}$-carboorganic radical or a $C_1$–$C_{30}$-organosilicon radical and Y is a $C_1$–$C_{20}$-organic group which connects E to $C^1$, L is a formally anionic or uncharged ligand, or identical or different ligands of this type, n is an integer from 0 to 7, m is an integer from 1 to 8.

12. A catalyst or catalyst system comprising a tripod metal complex as claimed in claim 11.

13. A process for stoichiometric or catalytic carbon-carbon bond formation or hydrogenation wherein a tripod metal complex as claimed in claim 11 is used.

14. A tripodal cyclopentadiene derivative of formula (I) as claimed in claim 1, wherein Z is cyclopentadienyl.

15. A tripodal cyclopentadiene derivative of formula (I) as claimed in claim 1, wherein Z is indenyl.

16. A tripodal cyclopentadiene derivative of formula (I) as claimed in claim 1, wherein Z is fluorenyl.

* * * * *

UNITED STATES PATENT AND TRADEMARK OFFICE
CERTIFICATE OF CORRECTION

PATENT NO. : 6,166,234
DATED : December 26, 2000
INVENTOR(S) : HUTTNER et al.

Page 1 of 2

It is certified that error appears in the above-identified patent and that said Letters Patent is hereby corrected as shown below:

Col. 37, claim 4, line 60, after "as" insert --claimed in--.

Col. 37, claim 5, line 63, after "derivative" insert --as claimed in--.

Col. 38, claim 6, line 32, "$C_5\text{-}C_{50}\text{-}$" should be --$C_5\text{-}C_{50}\text{-}$--.

Col. 38, claim 7, line 66, after "carboorganic" insert --radical--.

Col. 39, claim 7, line 5, "$C_5\text{-}C_{50}\text{-}$" should be --$C_5\text{-}C_{50}\text{-}$--.

Col. 40, claim 9, line 7, "$C_5\text{-}C_{50}\text{-}$" should be --$C_5\text{-}C_{50}\text{-}$--.

UNITED STATES PATENT AND TRADEMARK OFFICE
CERTIFICATE OF CORRECTION

PATENT NO. : 6,166,234
DATED : December 26, 2000
INVENTOR(S) : Huttner et al.

It is certified that error appears in the above-identified patent and that said Letters Patent is hereby corrected as shown below:

Col. 40, claim 11, line 23, "tripod" should be --tripodal--.

Col. 40, claim 11, line 48, "Ad" should be --a--.

Col. 40, claim 8, line 54, "$C_5-C_{50}$-" should be --$C_5-C_{50}$- --.

Col. 41, claim 12, line 1, "tripod" should be --tripodal--.

Col. 41, claim 13, line 4, "tripod" should be --tripodal--.

Signed and Sealed this

Twenty-ninth Day of May, 2001

Attest:

NICHOLAS P. GODICI

Attesting Officer

Acting Director of the United States Patent and Trademark Office